(12) United States Patent
Roberts et al.

(10) Patent No.: US 11,389,269 B2
(45) Date of Patent: Jul. 19, 2022

(54) PORTABLE MEDICAL GRADE AIR PURIFICATION SYSTEM

(71) Applicant: AtmenBio, LLC, Plano, TX (US)

(72) Inventors: Justin L. Roberts, Oak Ridge, NC (US); Brian Dean Owens, Plano, TX (US)

(73) Assignee: AtmenBio, LLC, Plano, TX (US)

( * ) Notice: Subject to any disclaimer, the term of this patent is extended or adjusted under 35 U.S.C. 154(b) by 0 days.

(21) Appl. No.: 17/317,703

(22) Filed: May 11, 2021

(65) Prior Publication Data

US 2021/0346120 A1 Nov. 11, 2021

Related U.S. Application Data

(60) Provisional application No. 63/023,010, filed on May 11, 2020.

(51) Int. Cl.
| | |
|---|---|
| *A61L 9/00* | (2006.01) |
| *A61L 2/00* | (2006.01) |
| *A62B 7/08* | (2006.01) |
| *A61B 90/40* | (2016.01) |
| *A61L 9/03* | (2006.01) |
| *A61L 9/20* | (2006.01) |

(52) U.S. Cl.
CPC ............ *A61B 90/40* (2016.02); *A61L 9/032* (2013.01); *A61L 9/20* (2013.01); *A61B 2090/401* (2016.02); *A61L 2209/134* (2013.01); *A61L 2209/14* (2013.01)

(58) Field of Classification Search
CPC ............ A61L 9/014; A61L 2209/111; A61L 2209/12; A61L 2209/14; A61L 9/20; B01D 46/442; B01D 46/0028; B01D 46/0036

USPC .............................................. 422/4, 24, 121
See application file for complete search history.

(56) References Cited

U.S. PATENT DOCUMENTS

| | | |
|---|---|---|
| 3,757,495 A | 9/1973 | Sievers |
| 4,810,269 A | 3/1989 | Stackhouse et al. |
| 9,310,088 B2 | 4/2016 | Melikov et al. |

(Continued)

FOREIGN PATENT DOCUMENTS

| | | |
|---|---|---|
| EP | 3473941 A1 | 4/2019 |
| WO | 9428814 A1 | 12/1994 |

OTHER PUBLICATIONS

Kim et. al., 2018, Inactivation of airborne viruses using vacuum ultraviolet photocatalysis for a flow-through indoor air purifier with short irradiation time, Aerosol Science and Technology (52), 557-566.

(Continued)

*Primary Examiner* — Monzer R Chorbaji
(74) *Attorney, Agent, or Firm* — Goodhue, Coleman & Owens, P.C.

(57) ABSTRACT

A system, method, and air purification device. Air is taken in from an environment into the air purification system. The air is prefiltered. The air is filtered with a primary filter. The filtered air is treated with vacuum ultraviolet radiation in a primary reaction chamber to generate irradiated air. The irradiated air is treated with ultraviolet-C radiation in a secondary reaction chamber to remove ozone. Ozone and other contaminants are removed from the irradiated air utilizing a carbon filter to generate purified air. The purified air is emitted back into the environment from the air purification system.

20 Claims, 18 Drawing Sheets

(56) References Cited

U.S. PATENT DOCUMENTS

| | | | |
|---|---|---|---|
| 2004/0166037 A1 | 8/2004 | Youdell et al. | |
| 2005/0211415 A1* | 9/2005 | Arts | F24F 1/04 |
| | | | 165/59 |
| 2007/0266855 A1* | 11/2007 | Fleisher | B03C 3/32 |
| | | | 96/16 |
| 2010/0095844 A1* | 4/2010 | Gilleland | B01D 46/0036 |
| | | | 95/148 |
| 2010/0260644 A1* | 10/2010 | Day | A61L 9/205 |
| | | | 422/121 |
| 2011/0223071 A1* | 9/2011 | Kang | B01D 46/0036 |
| | | | 422/169 |
| 2017/0072082 A1* | 3/2017 | Jurak | A61L 9/22 |
| 2017/0080373 A1* | 3/2017 | Engelhard | B01D 46/442 |

OTHER PUBLICATIONS

Vatansever et al., 2013, Can biowarfare agents be defeated with light?, Virulence 4:8, 796-825.

* cited by examiner

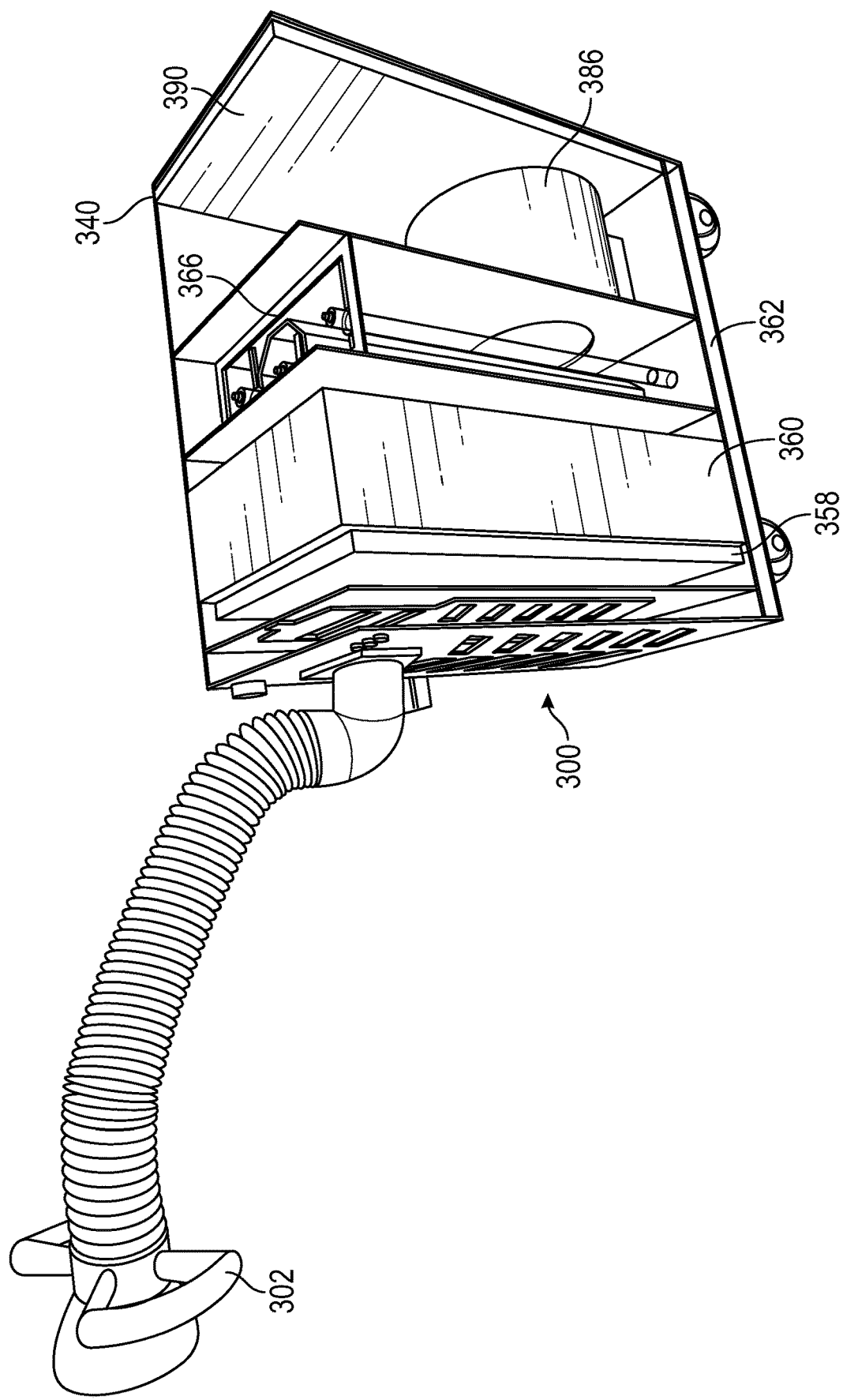

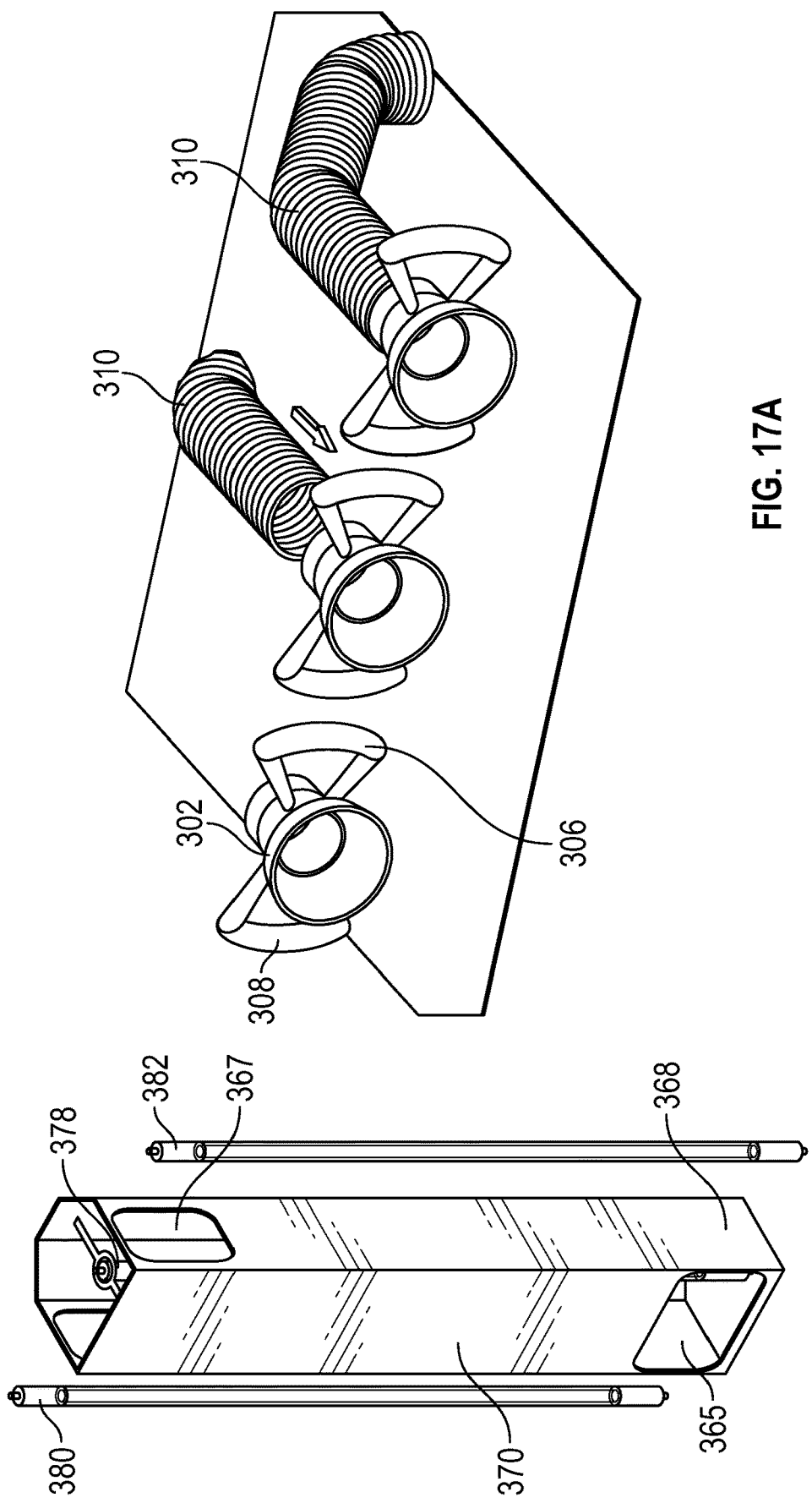

PORTABLE MEDICAL GRADE AIR PURIFICATION SYSTEM

PRIORITY STATEMENT

This application claims priority to U.S. Provisional Patent Application No. 63/023,010 filed on May 11, 2020 all of which is hereby incorporated by reference in their entirety.

BACKGROUND

I. Field of the Disclosure

The illustrative embodiments relate to air filtration. More specifically, but not exclusively, the illustrative embodiments relate to a system, method, and apparatus for extensive filtering of air particles in a medical, dental, or other environment.

II. Description of the Art

Recent events have emphasized the important of protecting dentists, doctors, nurses, hygienists, patients, and other individuals from airborne microorganisms, viruses, pathogens, contaminants, and other dangerous aerosolized fluids and particulates. It is particularly important to protect healthy individuals from the flu (e.g., H1N1, H5N1, swine influenza, bird influenza, and emerging strains, etc.), COVID-19, biological weapons (e.g., anthrax, small pox, etc.), and other dangerous agents whether natural or man-made. The emergence of COVID-19 has shown the risks, conditions, and liabilities that medical professionals, businesses, organizations, and individuals are subject to. Many devices that have attempted to address air filtering, purification, and/or sterilization have been unable to effectively address the smallest particles in a format that is user friendly. For example, many are bulky, awkward, or hard to position while others do not effectively filter or sterilize many of the smallest and most dangerous microorganisms and particulates in a single pass. Other filtration devices are too large or cost prohibitive to be physically and financially accessible to most individuals, businesses, medical and dental practices, or other groups.

SUMMARY OF THE DISCLOSURE

The illustrative embodiments provide a medical grade air purification system, method, and device. One embodiment provides a system, method, and air purification device. Air is taken in from an environment into the air purification system. The air is prefiltered with a prefilter. The air is filtered with a primary filter to generate filtered air. The filtered air is treated with vacuum ultraviolet radiation in a primary reaction chamber to generate irradiated air. The irradiated air is treated with ultraviolet-C radiation in a secondary reaction chamber to remove ozone and contaminants. The ozone and the contaminants are removed from the irradiated air emitted from the secondary reaction chamber utilizing a carbon filter to generate purified ar. The purified air is emitted back into the environment from the air purification system.

The illustrative embodiments provide an air purification system. The air purification system includes a frame housing various components, the frame is mounted to a plurality of casters for moving the air purification system between locations. The air purification system further includes a hose extending from an inlet of the frame, the hose is fixably positioned in three-dimensional space for suctioning air from an environment. The air purification system further includes a prefilter attached to the inlet for receiving the air from the environment. The air purification system further includes a primary filter proximate the prefilter that further filters the air. The air purification system further includes a primary reaction chamber housing a vacuum ultraviolet light that treats the air and associated contaminants. The primary reaction chamber is cylindrically shaped to maintain the air proximate the VUV light to generate irradiated air. The air purification system further includes a secondary reaction chamber interface with the primary reaction chamber, the secondary reaction chamber housing one or more ultraviolet-C lights for treating the irradiated air to remove ozone generated by the primary reaction chamber and to denature the contaminants. The air purification system further includes a fan that interfaces with the secondary reaction chamber to move the air through the air purification system. The air purification system further includes a carbon filter that interfaces with the fan to remove ozone and contaminants from the irradiated air.

In alternative embodiments, the hose includes a nozzle with two or more butterfly handles for positioning the hose. The nozzle may be covered with a moisture control barrier fitted to the nozzle that prefilters particulates and aerosols. The air purification system may exclude the hose to treat air in a residential or commercial environment. The air purification system may be attached to any number of other intake devices (e.g., hoses, mats, clothing, etc.). The air purification system may include a reaction chamber that houses the primary reaction chamber and the secondary reaction chamber. The primary reaction chamber may be nested in between portions of the secondary reaction chamber. The primary reaction chamber and secondary reaction chamber may be nested together or proximate each other. The nozzle may be covered with a disposable or washable moisture control barrier that prefilters particulates and aerosols. The primary filter may represent a HEPA or ULPA filter. The air purification system may be mounted on wheels or casters for easy movement. All or portions of the various components may be added or removed to different models of the air purification system. The primary reaction chamber may include multiple openings for dispersing the irradiated air into the secondary reaction chamber. The secondary reaction chamber may include two or more ultraviolet-C lights. A length and width of the primary reaction chamber may be associated with a time period for the air to be treated by VUV radiation from one or more VUV lights including the VUV light at approximately 180 nm. The time period may be at least 0.026 seconds. The air purification system may include a hinged top for easily replacing the prefilter, the primary filter, ultraviolet bulbs associated with VUV radiation and UVC radiation, and the carbon filter. The air purification system includes one or more catalysts for removing ozone from the irradiated air. The air purification system may include a power switch for turning the air purification system on and off. The air purification system may include a controller for controlling the flow rate of air through the air purification system in cubic feet per minute (or cubic meters per minute). The air purification system may include an interface for viewing and adjusting performance information of the air purification system, maintenance and cleaning reminders, and other relevant information. The air purification system may provide alerts regarding performance, maintenance, and repairs. The alerts may be sent directly or through one or more networks using a transceiver of the air purification system. The air purification system may include logic for tracking performance, maintenance, cleaning, and repairs of the air purification system. The air purification system may include one or more sensors for measuring contaminants in the purified air (e.g., viruses, ozone, etc.).

BRIEF DESCRIPTION OF THE DRAWINGS

Illustrated embodiments are described in detail below with reference to the attached drawing figures, which are incorporated by reference herein, and where:

FIGS. 3-12 are pictorial representations of an air purification system in accordance with an illustrative embodiment;

FIG. 16 is a pictorial representation of the nozzle and intake hose of FIGS. 3-12 in accordance with illustrative embodiments;

FIG. 17A-D are pictorial representation of portions of the air purification system of FIGS. 3-12 in accordance with illustrative embodiments;

DETAILED DESCRIPTION OF THE DISCLOSURE

Figure 1:
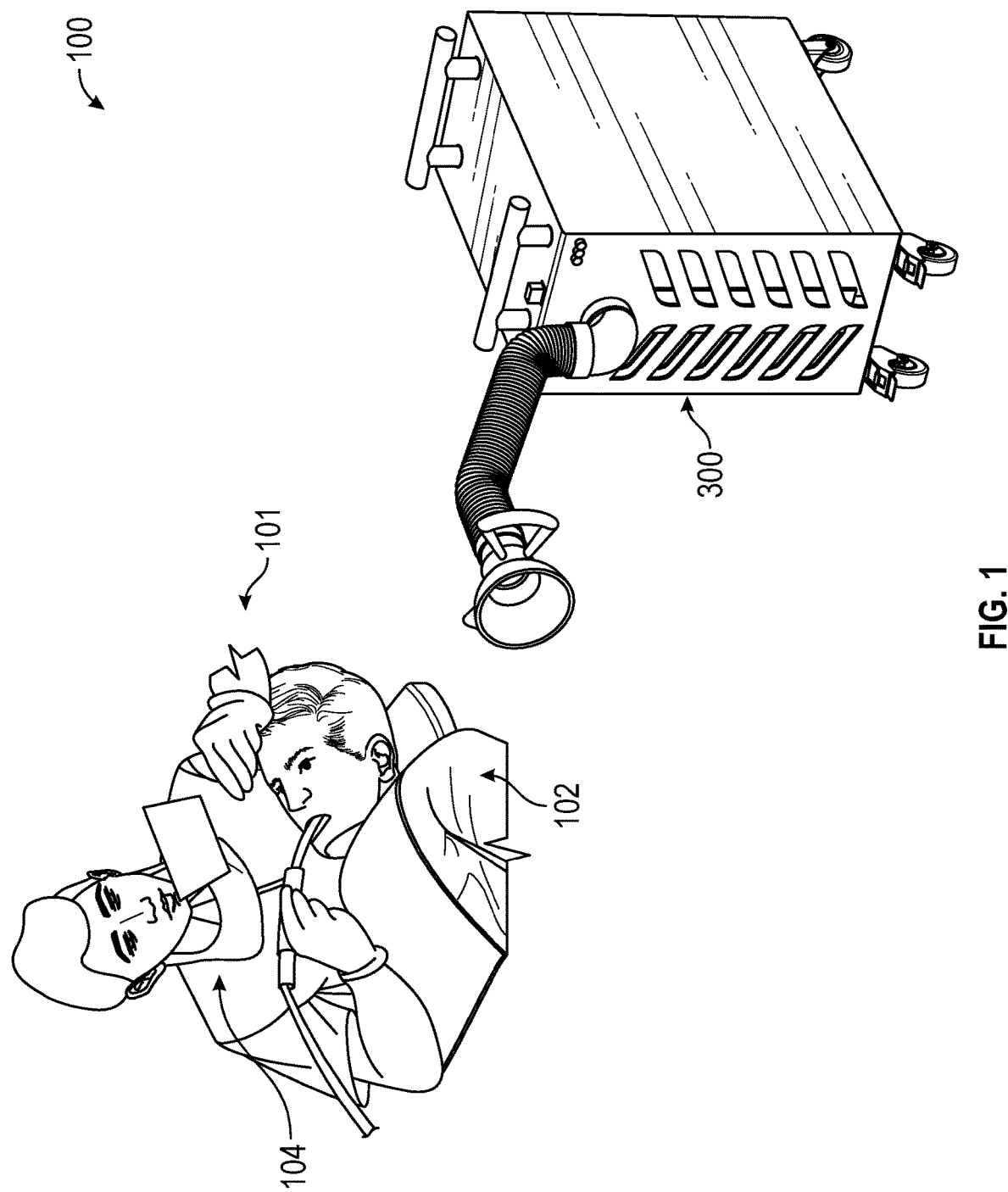
FIG. 1 is a pictorial representation of a medical environment in accordance with an illustrative embodiment.

The illustrative embodiments provide a single-pass air purification system that eliminates and eradicates airborne pathogens, contaminants, and microorganisms including bacteria and viruses. The illustrative embodiments utilize hospital grade HEPA or ULPA air filtration of bacteria and a vacuum ultraviolet (VUV) reaction chamber which denatures viruses in a single pass. The VUV reaction chamber utilizes high energy photons and ozone. The ozone is then subsequently catalyzed to generate clean oxygen using dual-pass UV-C technology and activated carbon. The UV-C light sources also continue to kill the pathogens. The carbon filter further eliminates volatile organic compounds, mold spores, and noxious odors. The illustrative embodiments may be referred to as an air filtering system, air filtering device, air purification system, air purification device, air treatment device, advanced filtering and ultraviolet irradiation system, air filtration and air purification system, or other similar terminology.

Unlike other filtering devices that rely on multiple passes to kill bacteria and denature viruses, the illustrative embodiments produce clean, safe air in the VUV chamber within approximately 0.026 seconds. For example, this means that a 1000 cubic foot room (10'×10'×10') may achieve clean air in four minutes on a high setting of 250 cubic feet of air flow per minute. This filtration is approximately ten times faster than existing portable filtering systems to significantly decrease the transmissibility of airborne pathogens in the healthcare environment. The length of the VUV chamber is associated with an air velocity/movement providing the sufficient amount of VUV exposure (i.e., 0.026s). The VUV light is effective at inactivation of viruses in a short time period (e.g., VUV photolysis, irradiation time, generating reactive oxidants, etc.) due to the high photon energy at 185 nm VUV light breaking down chemical bonds and disassociating the chemical bonds of the already filtered air. The application of UVC light further treats the air for contaminants and reactive oxidants.

The illustrative embodiments further provide a system, method, device, and apparatus for filtering air. The device may perform air filtering, purification, and sterilization using a number of pre-filters, multiple filters (e.g., ultra-low particulate air (ULPA) filters, high-efficiency particulate air (HEPA) filters, etc.) and ultraviolet (UV) lights to kill, neutralize, or sterilize air in any environment. The illustrative embodiments are configured to perform medical grade filtering and purification in a single pass rather than relying on multiple passes through the system to filter and deactivate applicable contaminants, such as viruses, bacteria, and other microorganisms.

The hose of the device may be positioned and is self-supporting. The hose may utilize any number of internally or externally supporting structures to be positioned proximate a patient, medical professional, treatment area, or so forth. As a result, the hose may be moved into a free-standing position extending from the air purification system near a patient, medical professional, or other user in the environment.

The air purification system may include any number of controls for turning the device on and off, setting the flow (e.g., low, medium, high, etc.), adjusting the light sources' intensity, activating/deactivating light sources, performing diagnostics (e.g., particulates, flow, ozone, power consumption, flow drops, electrical fluctuations, etc.), testing incoming/outgoing air/gases, calibrating the filtering system, and so forth. The air purification system may include a touch screen, switches, buttons, remote control, or a wireless interface (e.g., mobile application communicating through one or more transceivers to transceivers of the air purification system) for controlling the different components, features, and functions of the air purification system.

The air purification system may also include safety equipment, components, and features, such as fuse breakers, surge protectors, auto-shut off ballasts, fireproof materials, locking wheels/casters, anti-microbial surfaces, quick accessibility for repairs (e.g., hinged lid/top, access panel(s), etc.), maintenance, and replacements, or so forth to ensure the safety of the users and individuals proximate the air purification system.

The illustrative embodiments have particular applicability to addressing issues associated with viral and other outbreaks, such as the 2019 novel coronavirus referred to commonly as COVID-19, 2019-nCoV, or SARS-CoV-2. The illustrative embodiments provide for enhanced safety and treatment of various patients in dental offices, surgery centers, hospitals, waiting rooms, or other areas. The embodiments may also be utilized to protect individuals, families, and groups in any number of residential, commercial or other settings. The illustrative embodiments are mobile and highly effective in filtering and neutralizing various viruses, pathogens, and contaminants. The air purification system may be easily serviced to change or clean covers, hoses, prefilters, primary filters, fans, or carbon filters. Hinged openings and ports make the various components highly accessible. Seals and gaskets between the components keep everything sealed in an airtight fashion to prevent contamination between the various stages of treated air within the air purification system (e.g., disposable cover, prefiltered air, HEPA/ULPA filtered air, air treated with VUV ultraviolet radiation, air treated with UVC ultraviolet radiation, carbon filtered air, etc.). The shapes of the reaction chamber may vary slightly for enhanced manufacturing and implementation.

The various embodiments, description, functions, and Figures may be combined in any number of combinations and such combinations are expected regardless of limitations, restrictions, or divisionals created artificially or naturally.

FIG. 1 is a pictorial representation of a medical environment 100 in accordance with an illustrative embodiment. The medical environment 100 may represent any number of offices, rooms, clinics, spaces, or locations where medical procedures, surgeries, dental work, examinations, or other processes are performed. The medical environment 100 may be within a hospital, clinic, facility, building, mobile unit, or other structure. As with all medical environments, the goal, object, and design of the medical environment 100 is to keep a patient 102, a medical professional 104, and others safe and secure. The medical environment 100 may alternatively represent any number of commercial, residential, or other environments that may benefit from air purification and filtering.

The patient 102 may represent any number of individuals (human or animals) that are receiving treatment, assistance, help, or procedures. In some instances, multiple patients may be within the medical environment 100 at a time. The medical professional 104 may represent any number of doctors, dentists, surgeons, nurses, technicians, specialists, and other individuals whether professional or non-professional that may be providing treatment, operating, observing, or otherwise assisting the patient 102.

The air purification system 300 is configured, designed, and provided to filter, purify, and sterilize the air 101 within the medical environment 100. The air 101 includes all of the naturally occurring gases that humans typically inhale and exhale, whether indoors or outdoors, such as nitrogen, oxygen, argon, carbon dioxide, and other gases. The air 101 may also include manmade or introduced gases. The air 101 within the medical environment 100 also includes microorganisms, particulates, fluids, and aerosols that may come from the mouth, nose, orifices, skin, hair, or body of the patient 102 and the medical professional 104, animals/insects, plants/trees, living organisms, dust, objects, equipment, structures, or so forth. The air purification system 300 filters the air within the medical environment 100 to remove the potentially harmful microorganisms (e.g., viruses, bacteria, fungi, etc.), particulates, aerosols, or other contaminants that may be dangerous, unhealthy, harmful, or undesirable to the patient 102 and the medical professional 104.

The air purification system 300 is portable and may be moved from location to location within the medical environment 100. For example, the air purification system 300 may be moved between rooms associated with chairs of a dentist office as a dentist, hygienist, orthodontist, endodontist, or other dental professional (i.e., medical professional 104) is treating or assisting the patient 102. The air purification system 300 may include casters, wheels, sliders, rails, tracks, or other mechanisms that facilitate the movement of the air purification system 300 from location to location.

As is subsequently described, the air purification system 300 may include a hose and nozzle for positioning an intake of the air 101 as close as possible to the patient 102 and/or medical professional 104. As a result, the contaminants are extracted from the air 101 as close to the source (i.e., respiration, operation/procedure site, etc.) so that the contaminants do not spread throughout the entire medical environment 100. For example, the breath of a potential sick, infected, or otherwise contaminated patient 102 may be filtered almost immediately upon being exhaled. The same is equally true for the medical professional 104 and other individuals within the medical environment 100 regardless of whether they are sick, infected, or otherwise contaminated whether knowingly or unknowingly. The nozzle is hygienic and easily cleaned.

The air purification system 300 is configured to be easily moved and positioned. In one embodiment, the air purification system 300 is powered through a connection to a standard wall for convenience, such as a standard wall outlet (e.g. 120 V). However, the air purification system 300 may be configured to be powered by any number of power standards, wiring/interfaces, systems, or equipment available throughout the world. The air purification system 300 may also be battery-powered for environments where traditional power systems, connections, wiring, or networks are unavailable or inconvenient.

The air purification system 300 may utilize multiple intake modes to filter the medical environment 100. As previously described, the hose and nozzle may act as a directed intake for processing air within the medical environment that is proximate the patient 102 and/or the medical professional 104. The hose and nozzle provide a targeted or patient mode that may be utilized for the air purification system 300. The air purification system 300 may also be switched into an ambient or full environment mode. In this mode, vents of the air purification system 300 are utilized to intake air within the medical environment 100. The filtering process utilized by the air purification system 300 in the ambient mode is to filter all applicable air within the medical environment 100 without targeting a specific location, patient 102/medical professional 104, user, or other segment or section of the medical environment 100. As a result, the air purification system 300 may be utilized in various locations, manners, and functions to ensure patient safety, clean air for entire rooms, or otherwise process air 101. The modes may also be referred to as room, hygiene, and operative modes. The four scenarios in a dental office may be total room—half powered, total room—full powered, exam mode—half powered, and operative mode—full powered.

The air purification system 300 is configured to filter, purify, sterilize, or otherwise clean the air within the medical environment 100 utilizing a single pass. As a result, a standard sized room may be filtered within a matter of minutes because of the high volume of air flow that is filtered by the air purification system 300. Many existing systems do not sufficiently filter or treat the air within the medical environment 100 to remove the smallest and often the most dangerous microorganisms and contaminants. The illustrative embodiments apply the principles of established scientific principles regarding filtering and ultraviolet treatment of air 101 to ensure that harmful contaminants are removed from the medical environment utilizing the air purification system 300.

Unlike many existing systems, the air purification system 300 is configured to be easily serviceable by the medical professional 104, his or her staff, repair or maintenance persons, or other individuals with only rudimentary understanding of basic device maintenance. As a result, the overall cost, time, and effort associated with the air purification system 300 are reduced while maximizing the filtering results.

It is anticipated that the air purification system 300 may be utilized in various medical and nonmedical environments, such as to purify rooms, waiting rooms, nail salons, massage rooms, homes, business settings, offices, and other locations where highly purified air is necessary or desired. The illustrative embodiments may help prevent the spread of infectious diseases, particularly those that are airborne.

Figure 2:
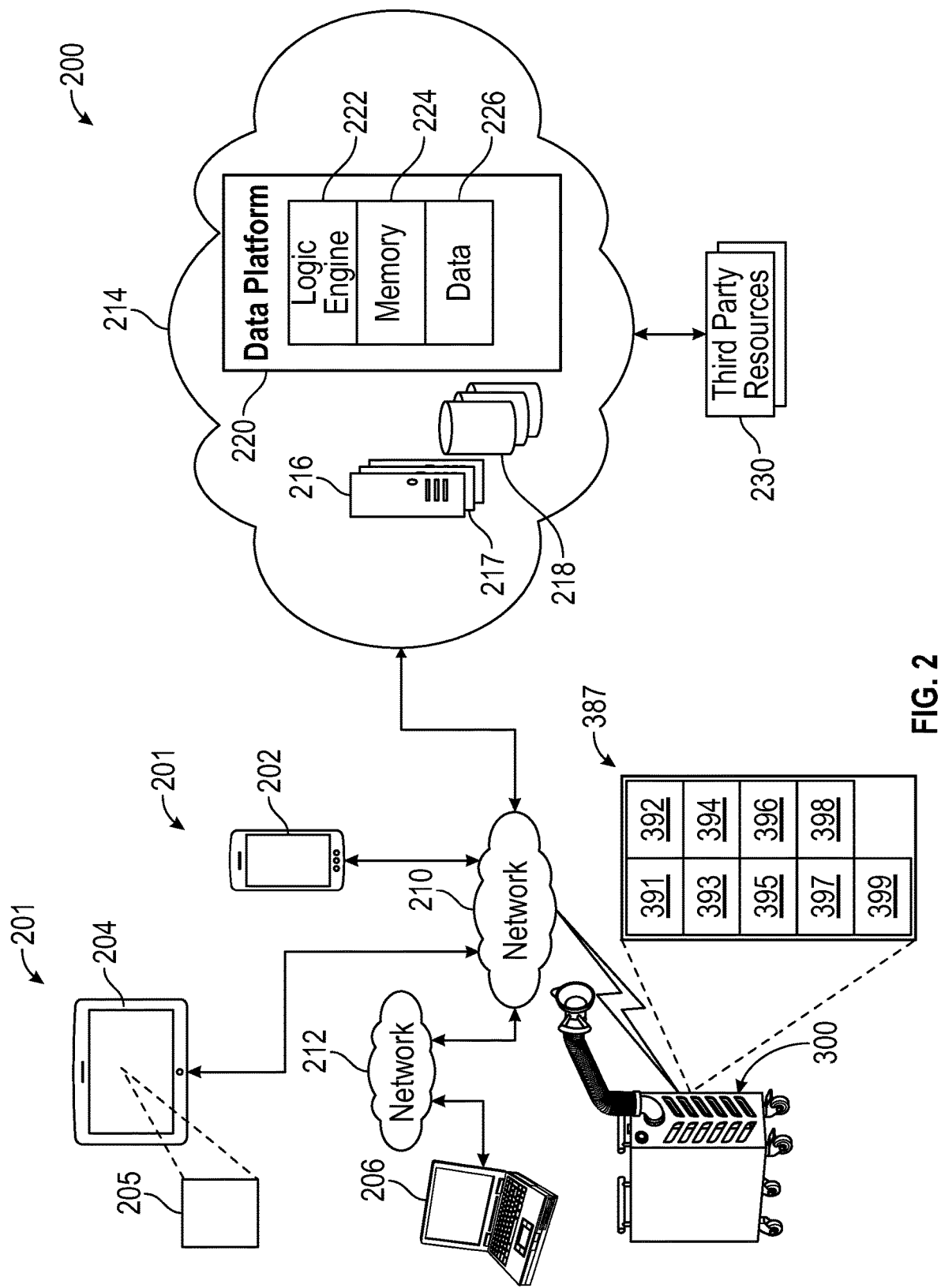
FIG. 2 is a pictorial representation of a system including an air purification system in accordance with an illustrative embodiment.

FIG. 2 is a pictorial representation of a system 200 including an air purification system 300 in accordance with an illustrative embodiment. In one embodiment, the system 200 of FIG. 2 may include any number of devices 201, networks, components, software, hardware, and so forth. In one example, the system 200 may include a wireless device 202, a tablet 204 displaying graphical user interface 205, a laptop 206 (altogether devices 201), a network 210, a network 212, a cloud system 214, servers 216, databases 218, a data platform 220 including at least a logic engine 222, a memory 224, and data 226. The cloud system 214 may further communicate with third-party resources 230. The various devices, systems, platforms, and/or components may work alone or in combination.

Each of the devices, systems, and equipment of the system 200 may include any number of computing and telecommunications components, devices or elements which may include processors, memories, caches, busses, motherboards, chips, traces, wires, pins, circuits, ports, interfaces, cards, converters, adapters, connections, transceivers, displays, antennas, operating systems, kernels, modules, scripts, firmware, sets of instructions, and other similar components and software that are not described herein for purposes of simplicity. For example, the software/applications or hardware may implement all or portions of the processes, methods, and embodiments described herein and shown in the Figures.

For example, the air purification system 300 may include electronics 387 including at least wiring 391, power systems 392, sensors 393, a transceiver 394, logic 395, a display 396, a power switch 397, a motor control switch 398, and a power cord 399. The wiring may include one or more power (e.g., AC, DC, etc.) and communications cords (e.g., serial, parallel, proprietary, etc.) for connecting the various components of the air purification system 300. The power systems 392 power the various components of the air purification system 300 including the electronics 387 and a fan (see FIGS. 3-12). The power systems 392 may connect to the power cord 399 for receiving electricity from a building, generator, structure, or other location. In one embodiment, the power cord 399 includes a magnetic interface or break away interface to the body of the air purification system 300 so that the power cord 399 may be removed from the air purification system 300 without tripping a user, damaging the air purification system 300, or otherwise causing damage to a user or the air purification system 300 itself. In one embodiment, portions of the wiring 391, power systems 392, and other electronics 387 may be run through the false bottom 362. The false bottom 362 (see FIG. 5) is a section near the bottom 342 of the frame 322 (or alternatively sides, back, or top) that separates and protects the various electronics 387.

The sensors 393 may be configured to sense the composition of the air before, during, and after the different stages of the purification process. In one embodiment, the sensors 393 include sensors that determine the levels of ozone that are being released by the air purification system to ensure that the air purification system 300 complies with local, State, and Federal laws, statutes, and practices as well as industry standards. The secondary chamber and other areas within the air purification system 300 may also include sensors 393. The sensors 393 may provide information that may be displayed to the user utilizing the display 396 or communicated through the transceiver 394. The transceiver 394 may communicate with any number devices to display the information utilizing a graphical user interface, browser, firmware, operating system/kernel, set of instructions, or an application.

The logic 395 is the processor, digital logic, and circuitry that processes information to implement the processes of the air purification system 300. The logic 395 may include a processor. The processor is the circuitry or logic enabled to control execution of a set of instructions. The processor may be one or more microprocessors, digital signal processors, application-specific integrated circuits (ASIC), central processing units, or other devices suitable for controlling the air purification system 300 including one or more hardware and software elements, executing software, instructions, programs, and applications, converting and processing signals and information, and performing other related tasks. The processor may be a single chip or integrated with other computing or communications elements. The logic 395 may also include a memory for storing information regarding the utilization (e.g., total hours on, logged hours, hours in each mode, etc.), air composition, environmental conditions (e.g., indoors, outdoors, etc.), networked devices, and so forth. The memory is a hardware element, device, or recording media configured to store data for subsequent retrieval or access at a later time. The memory may be a static or dynamic memory. The memory may include a hard disk, random access memory, cache, removable media drive, mass storage, or configuration suitable as storage for data, instructions, and information. In one embodiment, the memory and processor may be integrated. The memory may use any type of volatile or non-volatile storage techniques and mediums.

The transceiver 394 is a component comprising both a transmitter and receiver which may be combined and share common circuitry on a single housing. The transceiver 394 may communicate utilizing Bluetooth, Wi-Fi, cellular (i.e., 3G, 4G, 5G, PCS, GMSA, etc.), ZigBee, near field communications, wireless USB, Internet of things (IoT), infrared, mobile body area networks, ultra-wideband communications, or other radio frequency standards, networks, protocols, or communications. For example, the transceiver 394 may communicate directly with the wireless device 202 or through the network 210. The transceiver 394 may also send and receive the data 226 through the data platform 220.

The display 396 may communicate relevant information to the user regarding the operation and performance of the air purification system 300. The display 396 may communicate information processed by the sensors 393 and/or logic 396. For example, the display 396 may communicate total hours, hours per filter, ozone levels, air quality, air composition, ozone levels over time, maintenance and repair reminders (e.g., filter replacement, bulb replacement, etc.), and other applicable information. In one embodiment, the display 396 is a light emitting diode display. In another embodiment, the display 396 may also include one or more speakers, touch screens, or other interface components. For example, the display 396 may also be configured to receive input from the user for setting the mode of operation (i.e., targeted, ambient, etc.) and settings (e.g., high, low, air flow in cubic feet per minute (CFM), etc.).

The power switch 397 may be utilized to turn the air purification system off and on. The power systems 392 may include fuses and surge protectors for ensuring the safe operation of the air purification system 300. Unexpected power surges may be detected by the power systems 392 to turn off or otherwise protect the air purification system 300. The motor control switch 398 may be utilized to change the output of the air purification system (e.g., low, medium, high, etc.) or a custom output level. The power systems 392 may also include an induction power device or docking interface, such that when the body of the air purification system 300 is positioned on or above a generation unit, the air purification system is fully powered. A location may have multiple power generation pads or docking pads for powering the air purification system 300 when the air purification system 300 is moved to that location.

The system 200 may include any number of air purification systems, such as the air purification system 300. For example, multiple medical facilities and residential locations may all use the system 200. The system 200 may be utilized to process data 226 from numerous air purification systems 300. The data 226 may include information regarding particulates, allergens, ozone processing, chemical composition of processed air, weather, and so forth. The data 226 may be utilized to tune the performance of the air purification system 300 based on conditions such as humidity, air particulates (e.g., smoke, allergens, dust, etc.), known diseases/pathogens/viruses that are in season, and other applicable information.

In one embodiment, the system 200 may utilize any number of secure identifiers (e.g., passwords, pin numbers, certificates, etc.), secure channels, connections, links, virtual private networks, biometrics, or so forth to upload, manage, and secure the data 226. Various authentications and verifications may be performed to ensure that data 226 is true and accurate. The devices 201 utilize any number of applications, browsers, gateways, bridges, or interfaces to communicate with the cloud system 214, platform 220, and/or associated components. The devices 201 may include any number of Internet of Things (IoT) devices, home, and commercial devices.

The data 226 may include a number of different data types. The data 226 may include information and data for a number of different air purifications systems. The data 226 may specify information regarding operation, performance, ambient conditions, and so forth. For example, the data 226 stored by both the air purification system 300 and in the data platform 220 may specify total hours of operation, hours for each filter/bulb, ambient conditions (e.g., temperature, humidity, etc.), ozone levels (e.g., primary reaction chamber, secondary reaction chamber, expelled air, etc.), processed cubic feet of air (per minute, hour, day, week, year, all time, etc.), and other applicable information.

The wireless device 202, tablet 204, and laptop 206 are examples of common devices 201 that may be utilized to capture, receive, and manage data 226 as well as configure and operate the air purification system 300. For example, the various devices may capture data relevant to the air purification system 300 that is subsequently utilized or sent to the air purification system 300. Other examples of devices 201 may include e-readers, cameras, video cameras, electronic tags, audio systems, gaming devices, vehicle systems, kiosks, point of sale systems, televisions, smart displays, monitors, entertainment devices, medical devices, virtual reality/augmented reality systems, or so forth. The devices 201 may communicate wirelessly or through any number of fixed/hardwired connections, networks, signals, protocols, formats, or so forth. In one embodiment, the wireless device 202 is a cell phone that communicates with the network 210 through a 5G connection. The laptop 206 may communicate with the network 212 through an Ethernet, Wi-Fi connection, cellular, or other wired or wireless connection. The data 226 may be captured based on the permissions, authorization, and confirmation of the user associated with the air purification system 300. The data 226 may also include location-based information and weather information. The data 226 may be utilized to tune performance for each of a number of air purification systems.

The cloud system 214 may aggregate, manage, analyze, and process data 226 and across the Internet, networks 210, 212, other networks, and third-party resources 230. For example, the networks 210, 212 may represent any number of public, private, virtual, specialty (e.g., weather, allergy, etc.) or other network types or configurations. The different components of the system 200, including the devices 201 may be configured to communicate using wireless communications, such as Bluetooth, Wi-Fi, cellular communications, or so forth. Alternatively, the devices 201 may communicate utilizing satellite connections, Wi-Fi, 3G, 4G, 5G, LTE, personal communications systems, DMA wireless networks, and/or hardwired connections, such as fiber optics, T1, cable, DSL, high speed trunks, powerline communications, and telephone lines. Any number of communications architectures including client-server, network rings, peer-to-peer, n-tier, application server, mesh networks, fog networks, or other distributed or network system architectures may be utilized. The networks, 210, 212 of the system 200 may represent a single communication service provider or multiple communications services providers.

In one embodiment, the third-party sources 230 may monitor air quality in one or more medical, commercial, or residential environments utilizing the air purification system 300 to ensure compliance with applicable laws, regulations, standards, and best practices. In one embodiment, the cloud system 214 (or alternatively the cloud network) including the data platform 220 is specially configured to perform the illustrative embodiments and may be referred to as a system or platform.

The cloud system 214 or network represents a cloud computing environment and network utilized to aggregate, process, manage, search, verify, generate, and distribute data 226 and communicate with and control the air purification system 300 (based on applicable permissions and authorizations). The cloud system 214 allows data 226 and specified actions (e.g., warnings, communications, updates, configurations, etc.) from multiple businesses, users, managers, or service providers to be centralized. In addition, the cloud system 214 may remotely manage configuration, software, and computation resources for the devices of the system 200, such as devices 201.

The cloud system 214 may prevent unauthorized access to data 226, tools, and resources stored in the servers 216, databases 218, and any number of associated secured connections, virtual resources, modules, applications, components, devices, or so forth. In addition, a user may more quickly upload, aggregate, process, manage, view, and distribute data 226 (e.g., profiles, updates, surveys, content, etc.) where authorized, utilizing the cloud resources of the cloud system 214 and data platform 220.

The cloud system 214 allows the overall system 200 to be scalable for quickly adding and removing air purification systems, users, businesses, authorized sellers, analysis modules, distributors, valuation logic, algorithms, moderators, programs, scripts, filters, distribution partners, or other users, devices, processes, or resources. Communications with the cloud system 214 may utilize encryption, secured tokens, secure tunnels, handshakes, secure identifiers (e.g., passwords, pins, keys, scripts, biometrics, etc.), firewalls, digital ledgers, specialized software modules, or other data security systems and methodologies as are known in the art.

The servers 216 and databases 218 may represent a portion of the data platform 220. In one embodiment, the servers 216 may include a web server 217 utilized to provide a website, mobile applications, and user interface (e.g., user interface 205) for interfacing with numerous users. Information received by the web server 217 may be managed by the data platform 220 managing the servers 216 and associated databases 218. For example, the web server 217 may communicate with the database 218 to respond to read and write requests. For example, the servers 216 may include one or more servers dedicated to implementing and recording communications involving the data 226. For example, the databases 218 may store a record for updating information relating to data 226 from the air purification system.

The databases 218 may utilize any number of database architectures and database management systems (DBMS) as are known in the art. The databases 218 may store the available content associated with each air purification system 300 which may specify a date of purchase, product/service information (e.g., VUV bulbs, UVC bulbs, carbon filters prefilters, moisture control barriers, etc.), application, address, residential or commercial application, payment information, permissions, settings, location, cause preferences, cause restrictions, and so forth. Any number of secure identifiers such as passwords, pins, tones, codes, serial numbers, or so forth may be utilized to ensure that content, personal, or transaction information is not improperly shared or accessed.

The user interface 205 may be made available through the various devices 201 of the system 200. In one embodiment, the user interface 205 represents one or more of a graphical user interface, audio interface, tactile interface, or other interface that may be utilized to manage data, transactions, and other information. For example, the user may enter or update associated data for operating the air purification system 300 utilizing the user interface 205 (e.g., browser or application on a mobile device). The user interface 205 may be presented based on execution of one or more applications, browsers, kernels, modules, scripts, operating systems, or specialized software that is executed by one of the respective devices 201. For example, the user interface 205 may be programmed so that the air purification system 300 automatically turns on/off at specified times to specified operation levels.

The user interface 205 may display current and historical data as well as trends and projections for operation and performance of the air purification system 300. The user interface 205 may be utilized to set the user preferences, parameters, and configurations of the devices 201 as well as upload and manage the data, content, and implementation preferences sent to the cloud system 214. The devices 201 (e.g., displays, indicators/LEDs, speakers, vibration/tactile components, etc.) may present, play, display, or otherwise communicate the data 226 visually, audibly, tactilely, or any combination thereof.

In one embodiment, the system 200 or the cloud system 214 may also include the data platform 220 which is one or more devices utilized to enable, initiate, generate, aggregate, analyze, process, query, and manage data 226, and so forth with one or more communications or computing devices. The data platform 220 may include one or more devices networked to manage the cloud network and system 214. For example, the data platform 220 may include any number of servers, routers, switches, or advanced intelligent network devices. The data platform 220 may represent one or more web servers that perform the processes and methods herein described.

In one embodiment, the logic engine 222 is the logic that controls various algorithms, programs, hardware, and software that interact to receive, aggregate, analyze, rank, process, manage, score, communicate, and distribute data 226, content, transactions, alerts, reports, messages, or so forth. The logic engine 222 may utilize any number of thresholds, parameters, criteria, algorithms, instructions, or feedback to interact with users and interested parties and to perform other automated processes. In one embodiment, the logic engine 222 may represent a processor. The processor is circuitry or logic enabled to control execution of a program, application, operating system, macro, kernel, or other set of instructions. The processor may be one or more microprocessors, digital signal processors, application-specific integrated circuits (ASIC), central processing units, or other devices suitable for controlling an electronic device including one or more hardware and software elements, executing software, instructions, programs, and applications, converting and processing signals and information, and performing other related tasks. The processor may be a single chip or integrated with other computing or communications elements.

The memory 224 is a hardware element, device, or recording media configured to store data for subsequent retrieval or access at a later time. The memory 224 may be a static or dynamic memory. The memory 224 may include a hard disk, random access memory, cache, removable media drive, mass storage, or configuration suitable as storage for data 226, instructions, and information. In one embodiment, the memory 224 and logic engine 222 may be integrated. The memory 224 may use any type of volatile or non-volatile storage techniques and mediums.

In one embodiment, the cloud system 214 or the data platform 220 may coordinate the methods and processes described herein as well as software synchronization, communication, and processes. The third-party resources 230 may represent any number of human or electronic resources utilized by or in communication with the cloud system 214 including, but not limited to, businesses, entities, organizations (e.g., medical associations), individuals, government databases, private databases, web servers, research services, and so forth.

The third-party resources 230 may represent any number of electronic or other resources that may be accessed to perform the processes herein described. For example, the third-party resources 230 may represent government, private, and charitable servers, databases, websites, programs, services, and so forth for verifying the data 226. Any number of privacy and data policies may be implemented to ensure that applicable local, State, Federal, and International laws, standards, practices, and procedures are met.

In one embodiment, the logic engine 222 may utilize artificial intelligence and machine learning. The artificial intelligence and machine learning may be utilized to enhance data 226 and tune the performance of one or more air purification systems 300 based on applicable information (e.g., weather, disease outbreaks, contaminants, etc.).

In another embodiment, the devices 201 may include any number of sensors, appliances, and devices that utilize real time measurements and data collection to update the data 226. For example, a sensor network, wearables (e.g., watches, bands, implantable devices, etc.) and Internet of things (IOT) devices may gather user and ambient data. In one embodiment, the data platform 220 may extract data from third-party platforms by opting in and providing user credentials to various applications (e.g., Google, Amazon, eBay, Microsoft, etc.) the data platform 220 may extract data from the third party sources 230.

FIGS. 3-12 and 16-22 are pictorial representations of an air purification system 300 in accordance with an illustrative embodiment. FIGS. 3-10 show a partial cut away and exploded views of the air purification system 300 to better illustrate the various components, integration, functionality, and structure. As shown, the air purification system 300 may include a nozzle 302, a moisture control barrier 304, handles 306, 308, an intake hose 310, and airflow controller 314, air control plates 316, 318, a body 321, a frame 322, casters 332, caster locks 334, a hinge 336, a top 338, gaskets 340, bottom 342, side 344, 346, top handles 348, 350, vents 352, guides 354, 356, a prefilter 358, a primary filter 360, a false bottom 362, a reaction chamber inlet 364, a reaction chamber 366, a primary reaction chamber 368, a secondary reaction chamber 370, light ballasts 372, 374, 376, a vacuum ultraviolet (VUV) bulb 378, UVC bulbs 380, 382, a fan 386, a mounting plate 388, vibration mount 398, a carbon filter 390, wiring 391, power regulators 392, sensors 393, a transceiver 394, logic 395, a display 396, a power switch 397, a motor control switch 398, and a power cord 399.

The intake hose 310 is configured to receive air from the environment in a targeted or specific location or proximate one or more specified users. For example, when the air purification system 300 is operating in a targeted mode, all suction is channeled through the intake hose 310 and the associated nozzle 302. In one embodiment, the intake hose 310 is a self-supporting hose. The intake hose 310 may utilize a ribbon-lock construction to allow the hose to be positioned, shaped, and reshaped. The hose may be PVC with wire helix reinforcements for maintaining a position, orientation, and location. The intake hose 310 may be of any length desired for the selected user and application. In some embodiments, the intake hose 310 may be approximately 6 feet in length. The intake hose 310 and other portions of the air purification system 300 may be coated in any number of anti-bacterial, antifungal, or other disease resistant coatings, layers, or materials. In one embodiment, the intake hose 310 may include a string of ultraviolet lights or single flexible light that further treat the air as it passes through the extended length of the intake hose 310. As a result, the air may be further treated throughout the length of the intake hose.

The length and diameter of the intake hose 310 may be adjusted based on pressure applied by a user by hand or utilizing one or more tools. In another embodiment, the intake hose 310 may include any number of integrated or attached alms and motors for moving the intake hose 310 and corresponding nozzle 302 without the user touching the intake hose 310 or the nozzle 302. A processing system of the air purification system 300 may be utilized to move the intake hose 310 and associated nozzle 302 to the correct location. For example, all or portions of the air purification system 300 may be remotely operated utilizing a wireless or powerline connection to the air purification system.

The intake hose 310 further includes the nozzle 302. In one embodiment, the nozzle is configured to be positioned proximate one or more users (e.g., patient, doctor, nurse, person undergoing treatment, etc.). The nozzle 302 may include multiple handles 306, 308 for easily positioning the suction and of the hose 310. For example, two or more handles 306, 308 may allow a medical professional to easily manipulate the nose and attached intake hose 310. The nozzle 302 may attach to the intake hose utilizing an interference fit, snap, lock, pin, threads, or other attachment mechanism. The nozzle 302 and the intake hose 310 may be easily removed to be washed, autoclaved, or otherwise cleaned and sanitized. The nozzle 302 may define any number and size of openings for suctioning air within an environment. For example, the nozzle 302 may have a cone shaped opening to capture a significant amount of air within an area and to reduce noise created by suctioning the air into the nozzle 302 and intake hose 310. The size and shape of the nozzle 302 may vary based on the desired suction speed and tolerance for the associated noise. The nozzle 302 may be formed of any number of antibacterial plastics or other materials. The nozzle 302 is lightweight so that the intake hose 310 does not have significant leverage or moment aims caused by the nozzle 302.

The nozzle 302 may be fitted with a moisture control barrier 304. The moisture control barrier 304 may be utilized to prefilter large particles, aerosols, or moisture before being taken into the air purification system 300. The moisture control barrier 304 is configured to be autoclaved, washed, or replaced daily or as needed. The moisture control barrier 304 provides an inexpensive way to quickly and cheaply remove some of the largest particulates in the medical environment. The moisture control barrier 304 may include one or more elastics, buttons, straps, hooks, or other mechanisms for securely connecting to the nozzle 302. The moisture control barrier 304 fits the size and shape of the nozzle 302. The moisture control barrier 304 may be formed of an anti-bacterial, antifungal, or other materials, coatings, or components.

The intake hose 310 connects to the frame 322 or body 321 of the air purification system 300 at the intake port 312. The intake port 312 may be a fixed inlet for connecting to the intake hose 310. For example, the intake port may fit within or on the outside of the intake hose 310. In addition, any number of locking mechanisms, snaps, threads, tabs, releases, or other components may be utilized to secure the intake hose 310 to the intake port 312. In addition, the intake port 312 may be configured to rotate, pivot, or otherwise move to support the movement and positioning of the intake hose 310. The intake port 312 may similarly provide a resisted adjustment mechanism so that the intake port 312 and attached intake hose 310 do not move unless repositioned by a user.

The frame 322 is the support structure and housing for the air purification system 300. In one embodiment, the frame 322 may represent sheet metal that is molded into a rounded rectangular shape as shown. The frame 322 may be powder coated with any number of materials to improve the ability to clean and maintain the interior and exterior of the frame 322. The powder coating may be of a lighter color to ensure that it matches the other medical, dental, or operating equipment in the area and to make the air purification system 300 as aesthetically pleasing as possible. The lighter color of the exterior of the frame 322 may also show that the device is clean which is important in these types of environments. As previously described, the frame 322 is composed of a front 324, back 326, top 338, sides 344, 346, and a bottom 342 (all or a portion of which may be removed or accessed through screws, bolts, slide outs, or so forth). The frame 322 may also include the false bottom 362. The bottom 342 includes a number of casters 332. The casters 332 allow the air purification system 300 to be easily rolled from one location to another for more effectively positioning the air purification system including the intake hose 310 and the nozzle 302. The casters 332 may alternatively represent any number of wheels, rollers, slides, rail systems, pulleys, or so forth for moving, lifting, or otherwise positioning the air purification system 300. The top 338 may include top handles 348, 350. The top handles 348, 350 may be utilized to move the air purification system 300 from location to location. For example, a user may grab one or more of the top handles 348, 350 to roll the body 321 of the air purification system 300 into position.

The top 338 is attached to the back 326 utilizing a hinge 336. The hinge allows the top 338 to be hingedly opened to access the internal components of the air purification system for cleaning, tuning, maintenance, repairs, and replacement. Other portions of the frame 322 may be connected utilizing hinges, guides, slides, bolts, screws, rivets, or so forth. The top 338 further includes a latch 328 for securing the top to one or more of the front 324 or sides 344, 346. The top handle 348 may be utilized to lift the top 338 of the frame 322 once the latch 328 is released to access the internal components of the air purification system 300. The gaskets 340 may seal the various sections and components of the air purification system 300. For example, the gaskets 340 may seal the top 338 to the prefilter 358, primary filter 360, reaction chamber 366, and other components. The gaskets 340 may provide additional integrity for ensuring efficient sealing of the air purification system 300 to prevent unwanted air leakage.

Figure 4:
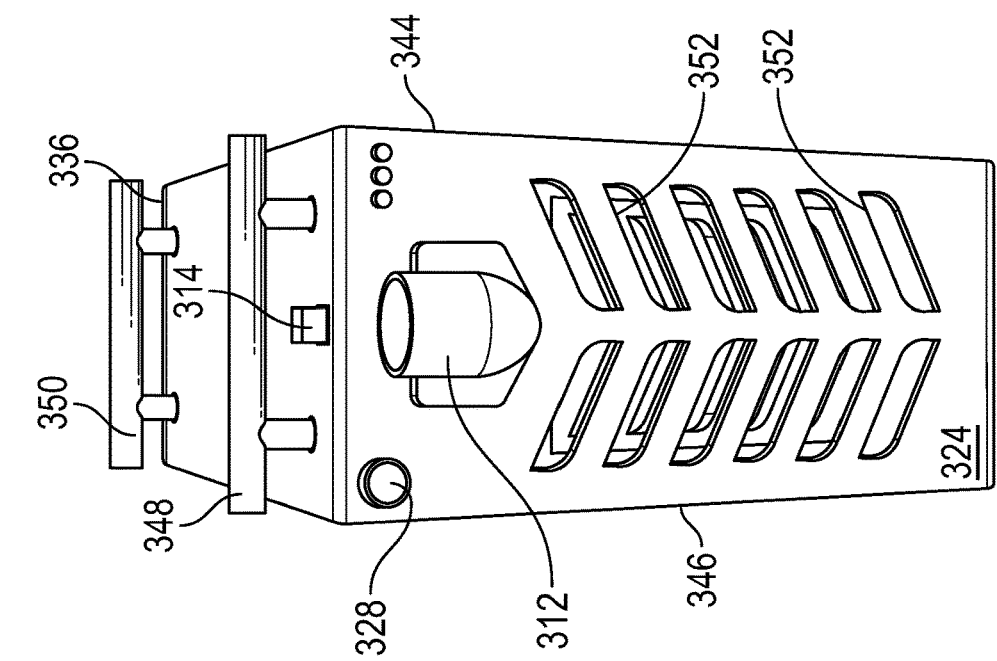
Figure 3:
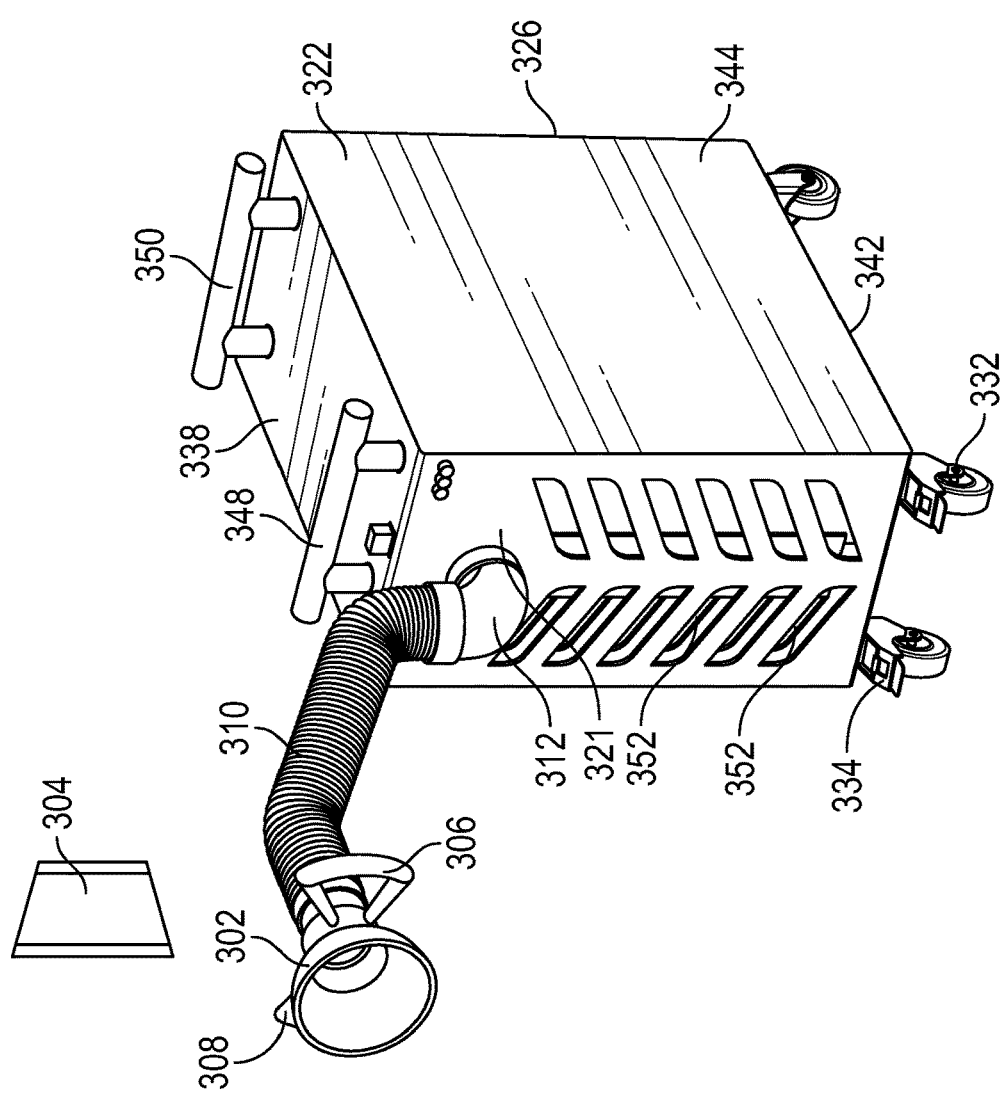

The air purification system 300 may also be configured to operate in an ambient mode. In one embodiment, the front 324 includes a number of vents 352. When the air purification system 300 is set to the ambient mode, the vents 352 are configured to allow airflow in and through the front of the air purification system 300. The vents 352 may be utilized for receiving ambient air from the environment. The vents 352 may be formed in any number of shapes including slits, rectangles, or decorative and functional patterns as are shown in FIGS. 3 and 4.

The airflow controller 314 may be utilized to control the mode of operation or air intake mode of the air purification system 300. The air flow controller 314 may connect to one or more intake control plates 316, 318 (see FIG. 6) that control the air flow into the air purification system. For example, when the air flow controller 314 is positioned to the up position as connected to the intake control plate 318 (see FIG. 4), the air in the environment is processed through the intake port 312 and intake hose 310. When the air flow controller 314 as connected to the intake control plate 318 is positioned to the down position, the air flow enters the frame through the vents 352. The intake control plates 316, 318 include openings 317, 319 associated with the intake port 312 and vents 352. When the intake port 312 and associated opening 317 are positioned to the up or top position based on movement of the air flow controller 314, the air purification system 300 suctions through the intake hose 310. When the air flow controller 314 and the opening 319 are positioned to the down or bottom position the air flow is through the vents 352. The vents 352 may be included on both the front 324 and back 326 of the frame 322 for taking in unpurified air and then expelling purified air.

The cut-away view of FIG. 5 further illustrates the configuration of the prefilter 358, primary filter 360, reaction chamber inlet 364, reaction chamber 366, fan 386, and the carbon filter 390. In one embodiment, a diffuser may be positioned after the intake control plates 316, 318 to further spread the air flow through the prefilter 358 and the primary filter 360. The diffuser may ensure that all portions of the prefilter 358 and the primary filter 360 experience similar wear and usage. The air scoop 362 may similarly channel the air to the reaction chamber inlet 364 on the backside of the primary filter 360.

Figure 7:
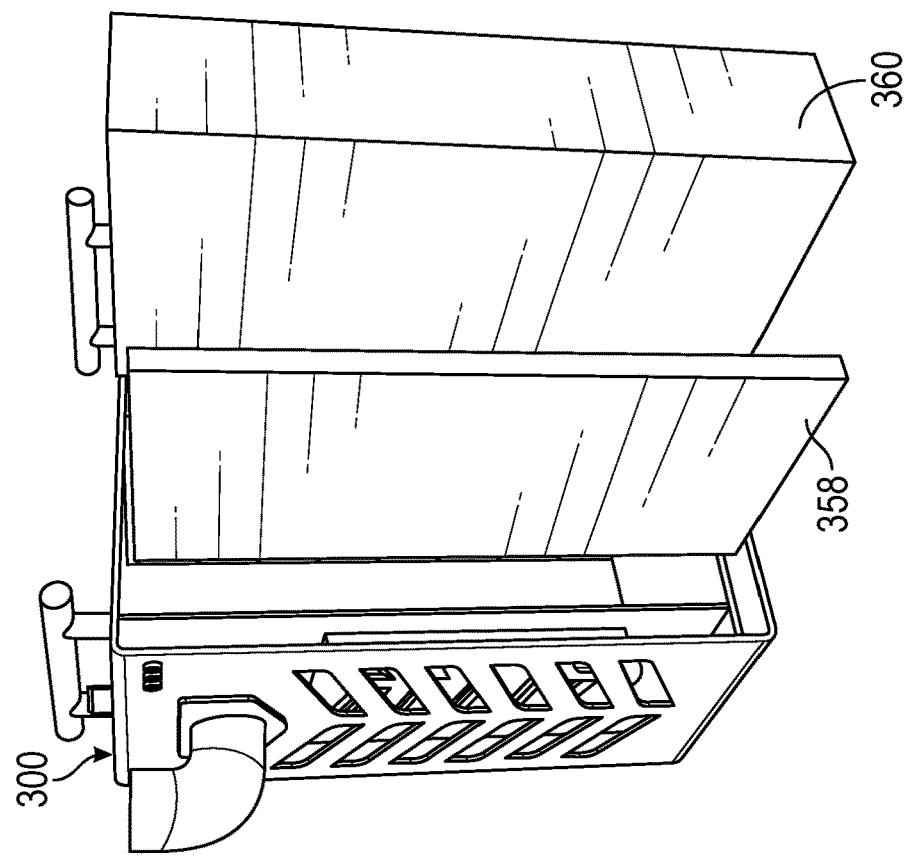
Figure 6:
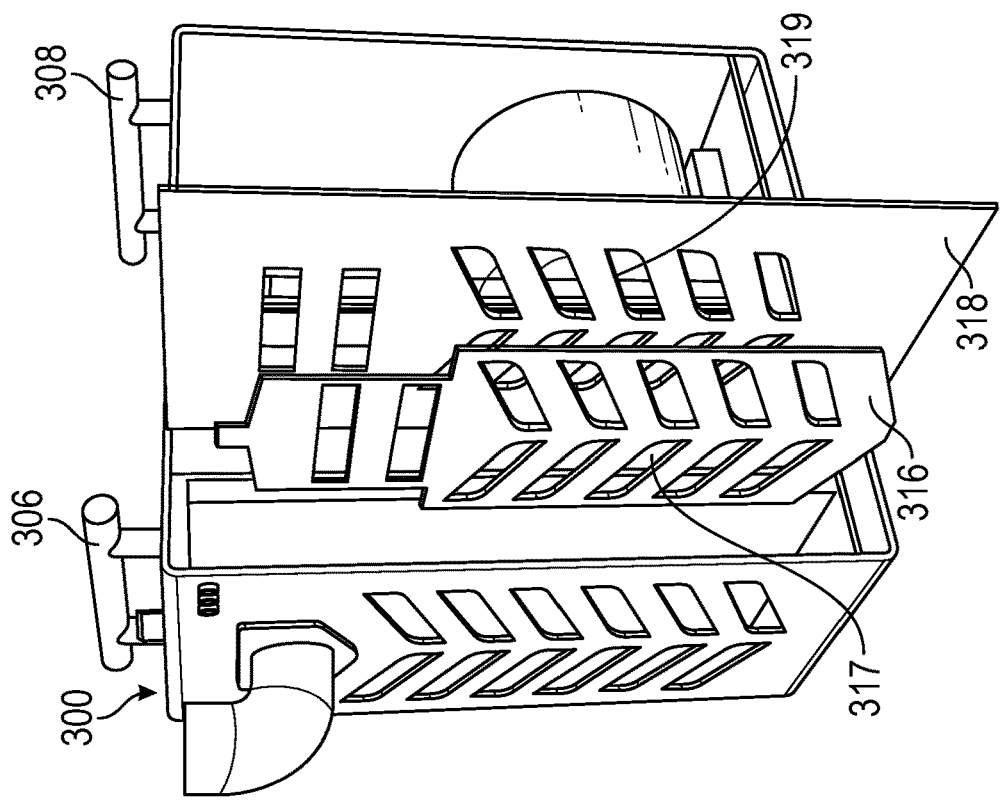

The filters are further shown in FIG. 7. The primary filter 360 may represent one or more high-end filters, such as a HEPA or ULPA filter. The air purification device 300 may be specially configured for applicable environments. The type of primary filter 360 used may vary based on the needed application. For example, the HEPA filter may be used for situations where airflow is prioritized as HEPA filters have better airflow than the incredibly dense ULPA filters. ULPA filters may be utilized when filtering all particulates (including those less than 0.1 micron) is the requirement or goal. ULPA filters may decrease the airflow through the air purification system 300 or may require a more powerful fan 386 and motor. In one embodiment, the prefilter 358 and primary filter 360 may be 12×24 inches. The width may be approximately 2 inches and 6 inches for the prefilter 358 and primary filter 360, respectively. In other embodiments, smaller filters may be utilized with the air flow channeled to the active portion of the filters. Any number of holders, positioners, or frames may also be utilized to secure the prefilter 358 and primary filter 360.

In one embodiment, the prefilter 358 and primary filter 360 may be associated with guides 354, 356 that properly align prefilter 358 and primary filter 360 within the frame 322. In one embodiment, the guides are thin metal protrusions, walls, or separators that extend from the sides 344, 346 of the frame 322. The guides 354, 356 appear as fins extending perpendicular to the sides 344, 346 when looking down on the guides 354, 356 from the top of the frame 322. As the air exits the primary filter 360 it is channeled by the guides 356, walls, or an air scoop to the reaction chamber inlet 364.

Figure 8:
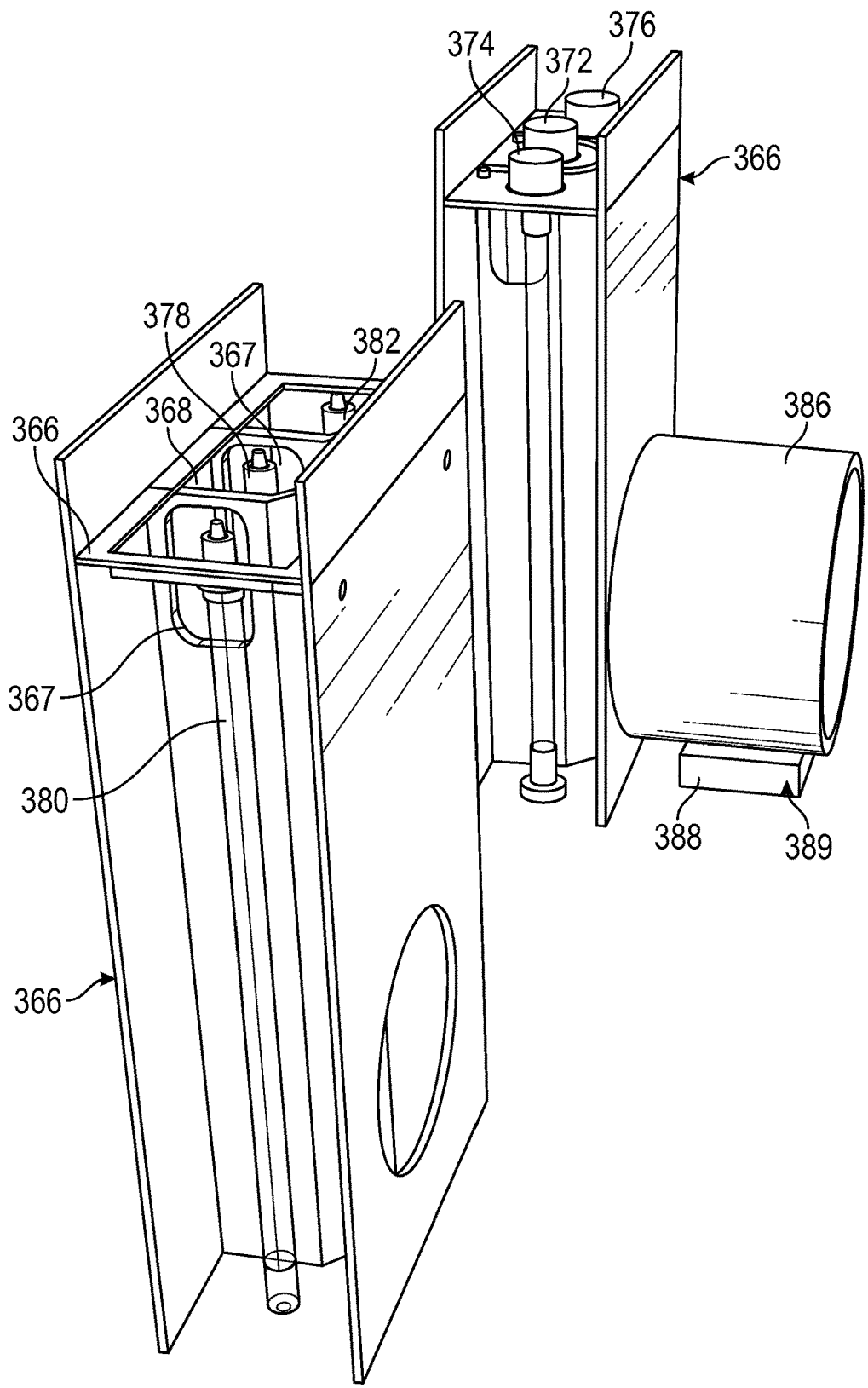
Figure 9:
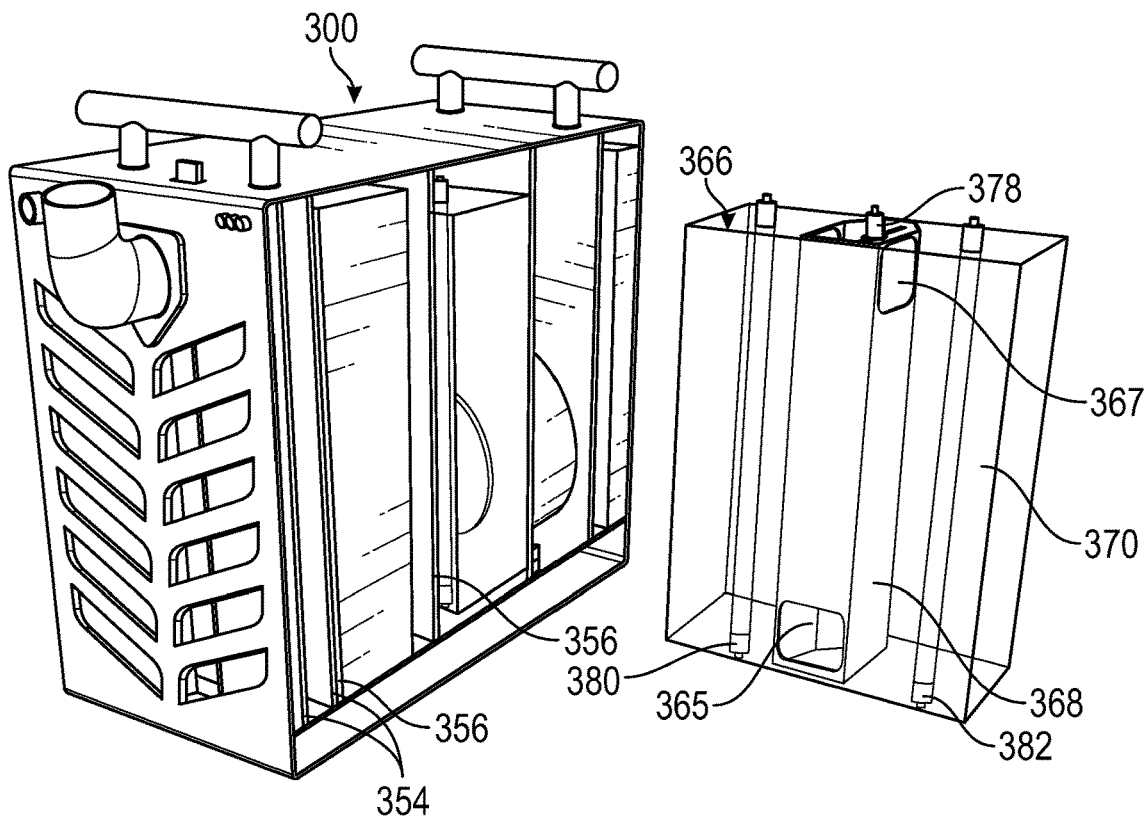
Figure 10:
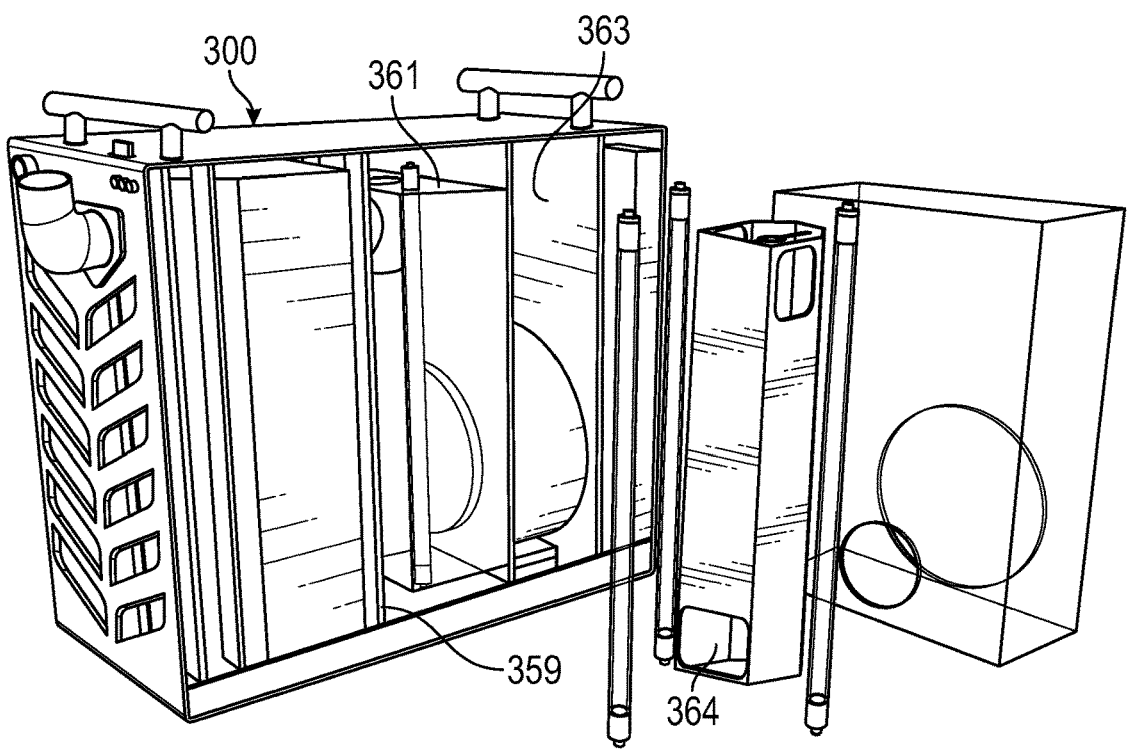
Figure 11:
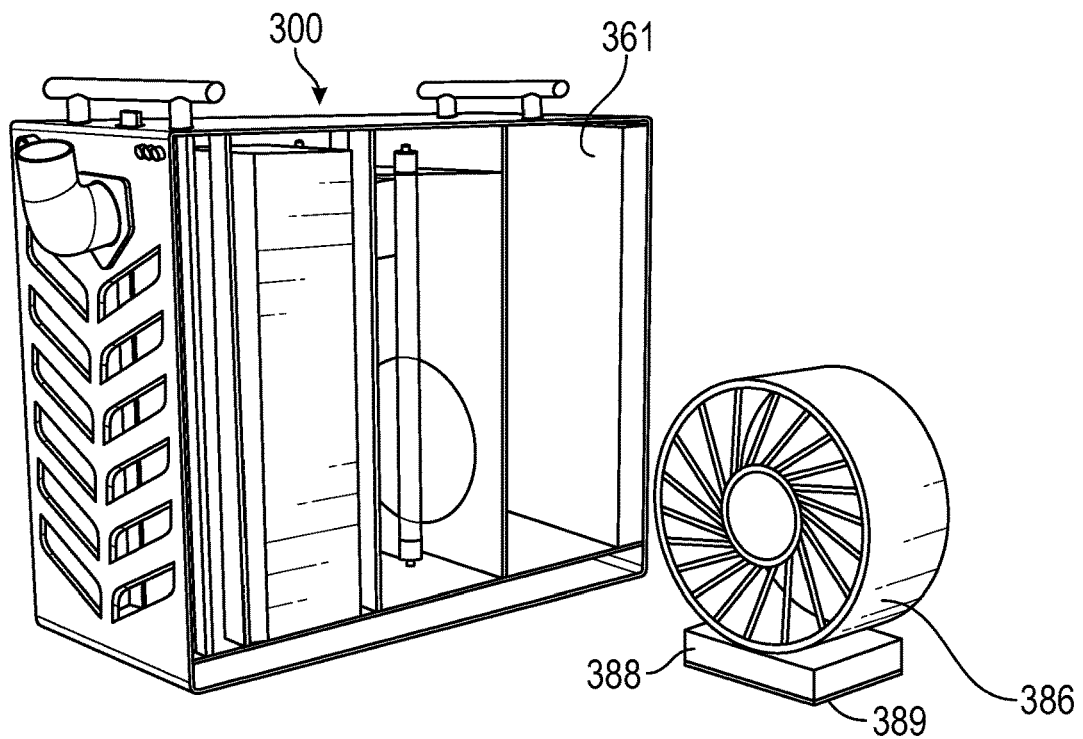
Figure 12:
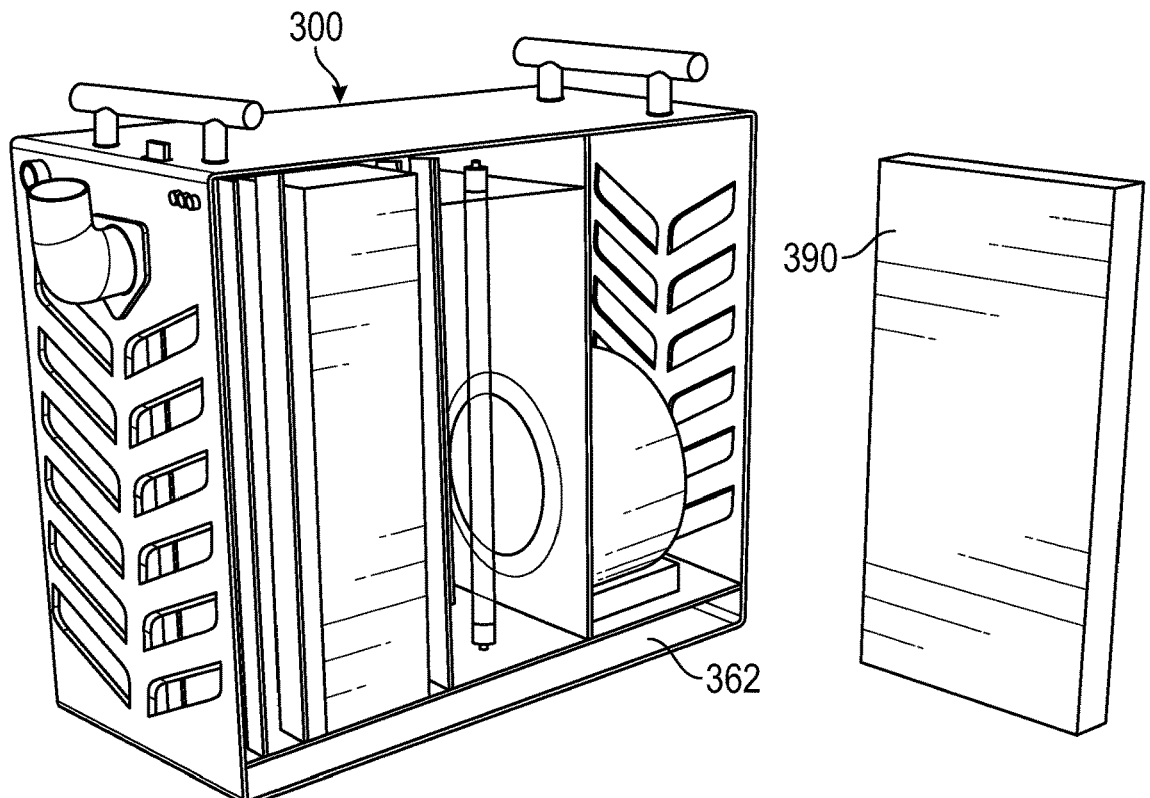

FIG. 8 further illustrates the reaction chamber 366. As shown the reaction chamber 366 includes the primary reaction chamber 368 shown as an extended component with opening 365 at the bottom of the primary reaction chamber 368 and openings 367 at the top of the primary reaction chamber 368. In one embodiment, the primary reaction chamber 368 may be a partially hexagonal or octagonal shape with another side of the primary reaction chamber 368 being rectangular, the two sides being integrated. In another embodiment, the primary reaction chamber 368 may be a cylinder or rectangle. The length of the reaction chamber 366 is sufficiently long to include the VUV bulb 378 and the UVC bulbs 380,382 and associated housing, mounting, and electronic components. The opening 365 is affixed to the primary reaction chamber inlet 368. For example, one or more mounting plates, collars, tabs, or other connectors may be utilized to secure the primary reaction chamber 368 to the reaction chamber inlet 364. The primary reaction chamber 368 houses at least one VUV bulb 378. The vacuum ultraviolet radiation emitted by the VUV bulb 378 emits radiation whose spectrum is approximately 185 nm. Many VUV bulbs emit 185 nm ultraviolet radiation that propagate effectively well through nitrogen in air, necessitating the need to keep the air in close proximity to the VUV bulb 378. The primary reaction chamber 368 performs ultraviolet photocatalytic oxidation (PCO). The VUV bulb 378 is ideal for disinfection of air because of the high efficiency for inactivating bacteria and protozoa. In particular, the VUV bulb 378 damages cell walls, membranes, enzymes, and nucleic acids of bacteria and damages virus proteins and genome of microorganisms in a very short time. The VUV bulb 378 may also generate ozone, hydroxyl radicals, and reactive oxygen species (ROS). The primary reaction chamber 368 is sized such that at an ideal airflow of 250 cfm, the microorganisms in the air are denatured while limiting the amount of ozone generated during the PCO process. Scientific research has shown that air (e.g., with contaminants, such as viruses) needs approximately 0.026 seconds be denatured by a VUV bulb 378. That would require that the primary reaction chamber 368 be at least twelve inches (12") long. To provide additional margins of error, the primary reaction chamber 368 may be approximately twenty inches long (20") providing the air within the reaction chamber approximately 0.046 seconds within the primary reaction chamber 368 where the VUV radiation may denature and sterilize the air particles from multiple angles.

The VUV bulb 378 is centered within the primary reaction chamber 368. As a result, the particles in the air are quickly denatured before being expelled through the openings 367 into the secondary reaction chamber 370. The primary reaction chamber 368 may be cylindrically shaped so that the airflow is evenly centered around the VUV bulb 378. In other embodiments, the primary reaction chamber 368 may be an extended rectangle. The openings 367 allow the air to dissipate the pressure in the primary reaction chamber 368 quickly for treatment in the secondary reaction chamber 370.

The secondary reaction chamber 370 may be rectangularly shaped with openings associated with the primary reaction chamber inlet and the fan outlet. The secondary reaction chamber 370 includes a number of UVC bulbs 380, 382. For example, one, two, four, eight, or more UVC bulbs 380, 382 may be mounted within the secondary reaction chamber 370 to treat the air expelled from the primary reaction chamber 368. In addition, UVC bulbs 380, 382 emit a wavelength that further degrades ozone. The UVC bulbs 380, 382 act as a photocatalyst to break down ozone that is generated by the VUV bulb 378 in the primary reaction chamber 368. Each of the VUV bulb 378 and the UVC bulbs 380, 382 are connected to light ballasts 372, 374, 376. The secondary reaction chamber 370 may include any number of fins, gates, or guides for guiding the airflow within the secondary reaction chamber 370, ensuring that there is time for the air to be treated by the UVC bulbs 380, 382. In one embodiment, the fins, gates, or guides may include or be coated with a catalyst for further neutralizing microorganisms and for degrading ozone. For example, the fins, gates, or guides may utilize a corrugated structure and may be composed of Pt, Pd, Ru, Cu, W, Sn, Rh, Ce, $Al_2O_3$, $SiO_2$, $TiO_2$, $ZrO_2$, metal oxides (e.g., manganese oxide, nickel oxide, iron oxide, etc.), and others. Any number of catalysts may be used within the air purification system 300 once the air is treated by the VUV bulb 378. The catalysts may be corrugated or otherwise structured to maximize surface area. Titanium palladium catalysts may be particularly helpful for treating the ozone and contaminants.

In one embodiment, the reaction chamber 366 may be coated with reflective materials, such as polished aluminum or other materials that reflect ultraviolet light, such that the air is treated from all sides (e.g., initially emissions, reflections, etc.). The reaction chamber 366 may also be described as the primary reaction chamber 368 housed within the secondary reaction chamber 370 to make effective use of space and quickly treat the air including all potential particles. The reaction chamber 366 is particularly effective at treating particles that are 0.3 microns or smaller including the smallest viruses.

The light ballasts 372, 374, 376 may fit one, all, or multiple bulbs of the air purification system 300. The light ballasts 372, 374, 376 may be powered by one or more power systems 392. The power systems 392 may include one or more amplifiers, regulators, transformers, and other applicable equipment for ensuring the safe electrical operation of the air purification system 300. The power systems 392 may provide power to the light ballasts 372, 374, 376 and the fan 386.

The reaction chamber 366 allows multiple different wavelengths of ultraviolet light to be applied to the air to both neutralize microorganisms and remove ozone and other radicals generated based on the operation of the VUV bulb 378. The reaction chamber 366 also efficiently utilizes space maximizing the time during which air is treated by the ultraviolet lights when flowing through the reaction chamber 366 while reducing the space required for airflow.

The air purification system 300 may further include separators 359, 361, 363. The separators 359, 361, 363 prevent unwanted airflow through the air purification system. One or more edges or openings defined by the separators 359, 361, 363 as shown may include seals, gaskets, or separators to ensure that there is not leakage of air between the various components of the air purification system 300 that are unwanted. The separator 359 separates the primary filter 360 from the reaction chamber 366. The reaction chamber 366 including the primary reaction chamber 368 and the secondary reaction chamber 370 may be removed from the frame 322 for maintenance and cleaning as needed.

The fan 386 is mounted to the bottom 342, sides 344, 346, or separators 361, 363 utilizing a mounting plate 388 and/or vibrations mounts 389 which may include a plate and rubber separator. The fan 386 is mounted to reduce the noise produced by the air purification system 300 based on noise, vibration, movement of air, and so forth. The fan 386 is industrial strength and provides the suction at the nozzle 302 and intake hose 310 that drives the airflow through the air purification system 300. The fan 386 is also powered by the power systems 392.

The fan 386 draws air from the reaction chamber 366 and expels the air into the carbon filter 390. The carbon filter 390 further removes microorganisms and the ozone generated by the interaction of the air with the VUV bulb 378. As a result, the ozone levels of the purified air leaving the air purification system 300 are negligible when expelled from the air purification system 300.

The carbon filter 390 includes carbon in a dust, microstructure, or compressed format that filters the air to remove contaminants as well as ozone. In one embodiment, the carbon filter 390 is a mesh receptacle for holding carbon (e.g., powder, particulates, etc.) that may be easily removed and replaced as needed. The carbon filter 390 may also include one or more screens, lattices, or additives that act as catalysts for neutralizing microorganisms, removing ozone, and degrading radical elements and compounds that may be created during the filtration process.

The carbon filter 390 may represent a single structure that has been compressed, adhered, molded, or otherwise generated or fixed as a single unit that may be added or removed from the air purification system 300. The carbon filter 390 may also have guides for easily adding and removing the carbon filter 390 from the air purification system 300.

It is expected that the prefilter 358, primary filter 360, VUV bulb 378, and UVC bulbs 380, 382, and carbon filter 390 will be replaced yearly to ensure effective operation.

Figure 13:
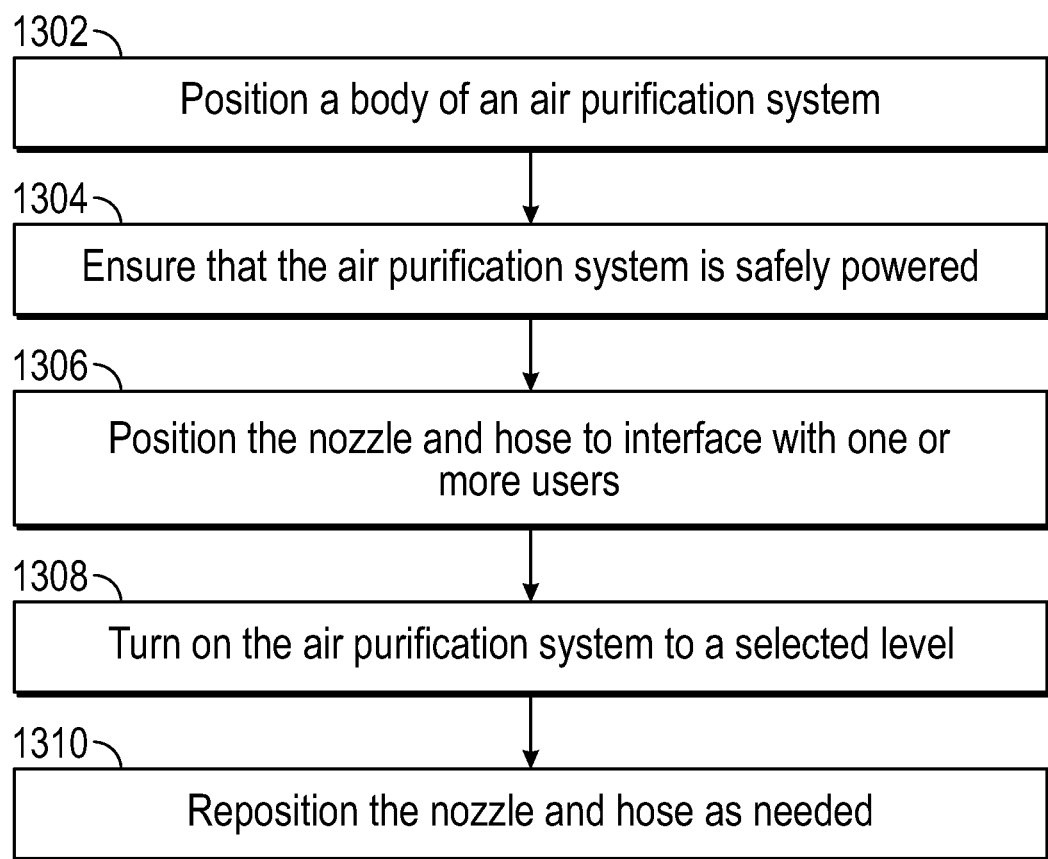
FIG. 13 is a flowchart of a process for configuring an air purification system in accordance with an illustrative embodiment.

FIG. 13 is a pictorial representation of a flowchart of a process for positioning an air purification system in accordance with an illustrative embodiment. The process of FIG. 13 may be performed by an air purification system, such as the air purification system 300 of FIGS. 3-12. In one embodiment, a user may perform the process of FIG. 13. In another embodiment, the air purification system may be equipped to handle audio/verbal, gesture, or other commands from the user to perform the process of FIG. 13. One or more remote controls or devices executing an application or web interface may also be utilized to control the air purification system.

The process may begin by positioning a body of the air purification system (step 1302). The body of the air purification system may represent the main structure and frame of the air purification system. The body is where the majority of the air filtering, purification, and sterilization processes are performed. The body may be mounted on casters, wheels, or rollers for easily moving the air purification system into place. The air purification system may also have handles that may be utilized to lift and/or move the air purification system from one point to another. In one embodiment, the air purification system may include a locking mechanism or stopper for fixing the air purification system at a single point. For example, locks of one or more castor wheels may ensure that the air purification system does not move or roll during utilization. The air purification system may alternatively use lifts, stops, kickstands, suction cups, magnets, or other devices for being fixed in place. In other embodiments, the air purification system may not include wheels or casters and may instead be semi-permanently positioned or fixed in place utilizing a plate, brackets, frame, or other mechanisms for securing the air purification system the floor, walls, ceiling, freely suspended, or so forth.

Next, the process continues by ensuring that the air purification system is safely powered (step 1304). In one embodiment, the air purification system may be powered through a standard 3-prong wall outlet (e.g., 120 V US outlet). The air purification system may also be powered by any number of standard or proprietary connections available within a hospital, clinic, dental office, mobile treatment unit, or other similar location. In alternative embodiments, the air purification system may be battery powered. The air purification system may also be powered by solar cells, fuel cells, hand crank, wind turbine, or other similar processes, systems, equipment, or so forth. In another embodiment, the air purification system may include a motion detector for automatically powering the air purification system on in response to detecting one or more users in the area. Similarly, the air purification system may turn itself off after not sensing any motion for a time period (e.g., five minutes).

Next, the process positions the nozzle and hose to interface with one or more users (step 1306). The hose is self-supporting and may be moved into any number of positions, locations, or orientations. The diameter and length of the hose may correspond to the needs of the user of the air purification system. In some instances, a 4-foot hose may be sufficient while in others an 8 foot or longer hose may be required. In one embodiment, the nozzle and hose may be proximate one or more users without being so close as to be disruptive, loud, annoying, in the way, or inconvenient. In other embodiments, the air purification system may include multiple hoses and nozzles for targeting numerous areas within a specific location at one time. For example, the hose may split in two for two patients that are near each other in the same room. The suction end of the hose and nozzle may also vary. In one embodiment, the hose may connect to a bib, collar, blanket, hat, vent, or other device worn or proximate the user.

Next, the process turns on the air purification system to a selected level (step 1308). The air purification system may include one or more levels for filtering and purifying the air. For example, the air purification system may have a low setting and a high setting. The air purification system may also be adjusted between multiple modes. For example, during step 1308, the air purification system may be set to a targeted mode that utilizes the hose and nozzle or to an ambient mode that utilizes vents on the front of the air purification system. Some variations of the air purification system may only be configured for utilizing the hose and nozzle or the integrated vents.

Next, the process repositions the nozzle and hose as needed (step 1310). The hose and nozzle may be moved or repositioned as needed based on the needs of one or more medical professionals, patients, or other users. For example, the medical professional may need to move from one location and/or position to another resulting in the need to similarly reposition the nozzle and hose. In addition, the body of the air purification system may also be rolled, positioned, moved, or maneuvered during step 1310.

Figure 14:
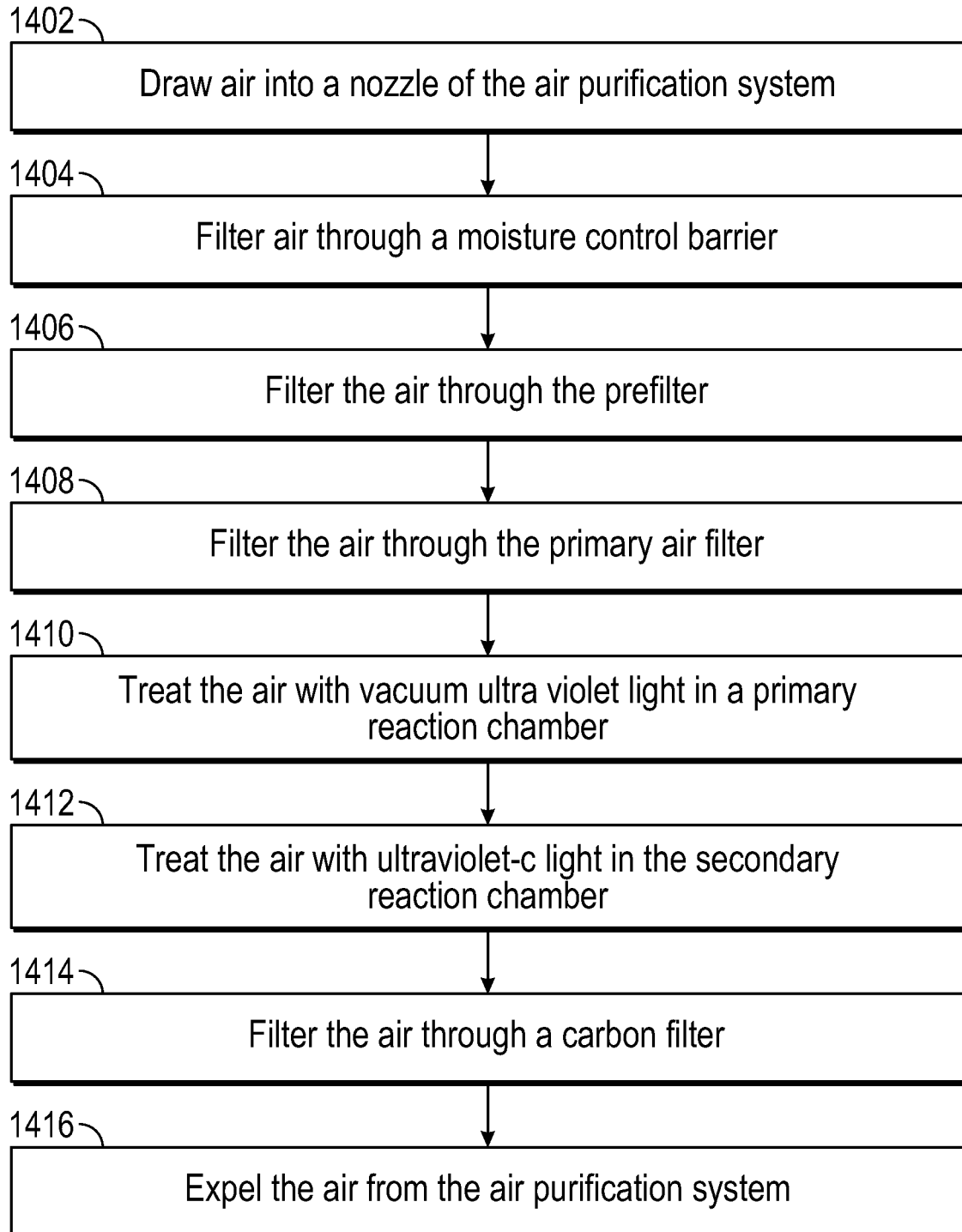
FIG. 14 is a flowchart of a process for purifying air utilizing an air purification system in accordance with an illustrative embodiment.

FIG. 14 is a flowchart of a process for purifying air utilizing an air purification system. The process of FIG. 14 may be performed by an air purification system, such as the air purification system 300 of FIGS. 3-12. The process may begin by drawing, air into a nozzle of the air purification system (step 1402). The air purification system may be powered by one or more fans, motors, or other devices that create suction and airflow through the air purification system. In an alternative embodiment, the airflow may be generated by one or more vacuums, central air systems, portable motors, or so forth. As previously disclosed, the nozzle may have numerous shapes, sizes, or interfaces for suctioning air from an environment. Targeted nozzles or larger vented attachments may also be utilized. In one embodiment, the hose of the air purification system may be compatible with nozzles typically used by vacuum cleaners, standard air filters, or other applicable devices.

Next, the air purification system filters air through a moisture control barrier (step 1404). The moisture control barrier may represent any number of cloth, paper, material, or other attachments that may be positioned over, on, or integrated with the nozzle and/or hose of the air purification system. The moisture control barrier is configured to be easily cleaned, autoclaved, or sanitized. Alternatively, the moisture control barrier may be disposed of and a new moisture control barrier utilized each day, for different patients, or so forth. The moisture control barrier may include any number of attachment components such as elastics, straps, buttons, hooks, hook-and-loop fasteners, adhesives, ties, or so forth.

Next, the air purification system filters the air through the prefilter (step 1406). The prefilter is configured to remove large particulates and organisms to better preserve the capacity of the main or primary filter. The prefilter may be more cheaply replaced as needed. For example, the main filters may represent HEPA or open filters that are much more expensive.

Next, the air purification system filters the air through the primary air filter (step 1408). The primary air filter may remove particles of varying size based on the application. In some embodiments more affordable filters may be utilized, as the primary filter because of the effectiveness of the UV treatments that are implemented by the air purification system. As a result, the air purification system is much cheaper than existing systems while still providing equivalent or better filtration results.

Next, the air purification system treats the air with vacuum ultraviolet light in a primary reaction chamber (step 1410). In one embodiment, the wavelength of the ultraviolet light may be approximately 185 nm for effectively degrading and breaking down even the smallest bacteria, viruses, and other bio contaminants. The VUV bulbs utilized may destroy the contaminants utilizing photonic emissions and ozone. The air purification system may utilize one or more reaction chambers with one or more VUV bulbs.

Next, the air purification system treats the air with ultraviolet-C light in the secondary reaction chamber (step 1412). In one embodiment, ultraviolet-C may be in the 200-280 nm wavelength. The secondary reaction chamber further sterilizes the air and degrades the ozone generated by the application of VUV light.

Next, the air purification system filters the air through a carbon filter (step 1414). The carbon filter further purifies the air and removes ozone. The carbon filter in step 1414 may represent a solid filter, carbon dust/particulates, or other composition. The air purification system may have a venting system for evenly or directionally venting the purified air. In another embodiment, scents or deodorizers may be introduced into the vented air as part of the air purification system.

Next, the air purification system expels the air from the air purification system (step 1416). The air purification system may be configured to purify between 50-500 cfm. In one embodiment, the air purification system processes air at approximately 250 cfm. The air quality of the air expelled, emitted, or otherwise communicated through the air purification system may be tested for ozone, composition, temperature, and other factors. In one embodiment, the air purification system may turn off completely or shut down the VUV bulb in response to determining the ozone levels are too high. For example, the air purification system may employ an automatic shut off in response to ozone levels exceeding 20 parts per billion (ppb).

In another embodiment, the intake hose may be connected to the outlet (closed loop) to ensure that the air purification system/device is fully sanitized. In another embodiment, the intake may also be preloaded with ozone utilizing an ozone generator or VUV bulb within or near the intake hose. In another embodiment, the air purification system may be covered with a plastic or material cover with openings for the vents on the front and back of the device. The cover may match the aesthetic of the location or may make the air purification system appear more desirable to children (e.g., elephant, giraffe, or anteater covers). In another embodiment, the air purification system may not include a fan/motor and may instead be powered as needed by a suction device, such as a common vacuum or central vacuum system. In another embodiment, the reaction chamber may be large enough to allow personal protective equipment, tools, or other materials to be placed within the air purification system for sterilization.

The illustrative embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments of the inventive subject matter may take the form of a computer program product embodied in any tangible or non-transitory medium of expression having computer usable program code embodied in the medium. The described embodiments may be provided as a computer program product, or software, that may include a machine-readable medium having stored thereon instructions, which may be used to program a computing system (or other electronic device(s)) to perform a process according to embodiments, whether presently described or not, since every conceivable variation is not enumerated herein. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions. In addition, embodiments may be embodied in an electrical, optical, acoustical or other form of propagated signal (e.g., carrier waves, infrared signals, digital signals, etc.), or wireline, wireless, or other communications mediums.

Computer program code for carrying out operations of the embodiments may be written in any combination of one or more programming languages, including an object-oriented programming language such as Java, Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a personal area network (PAN), or a wide area network (WAN), or the connection may be made to an external computer (e.g., through the Internet using an Internet Service Provider).

Figure 15:
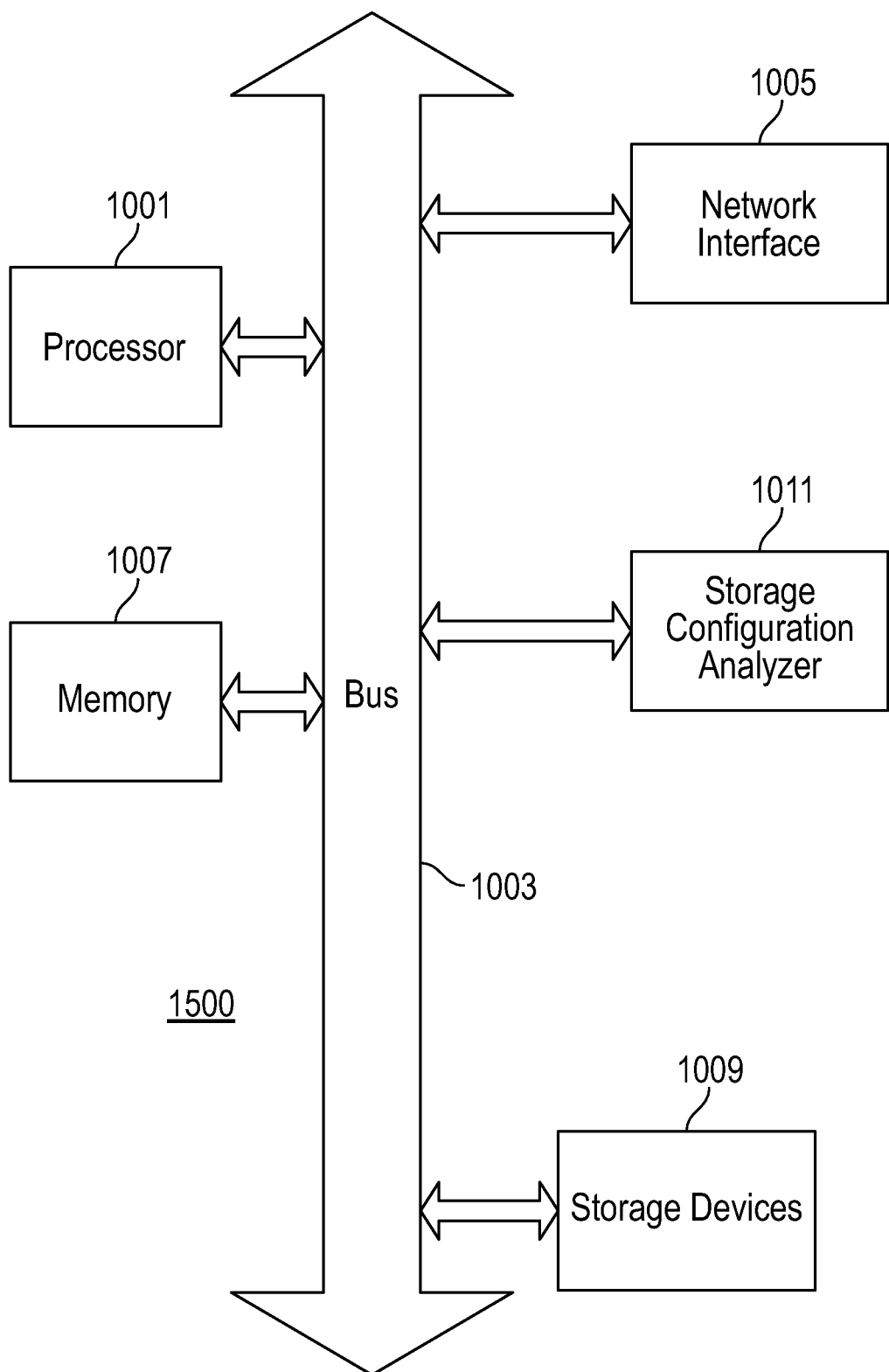
FIG. 15 depicts a computing system in accordance with an illustrative embodiment.
Figure 17D:
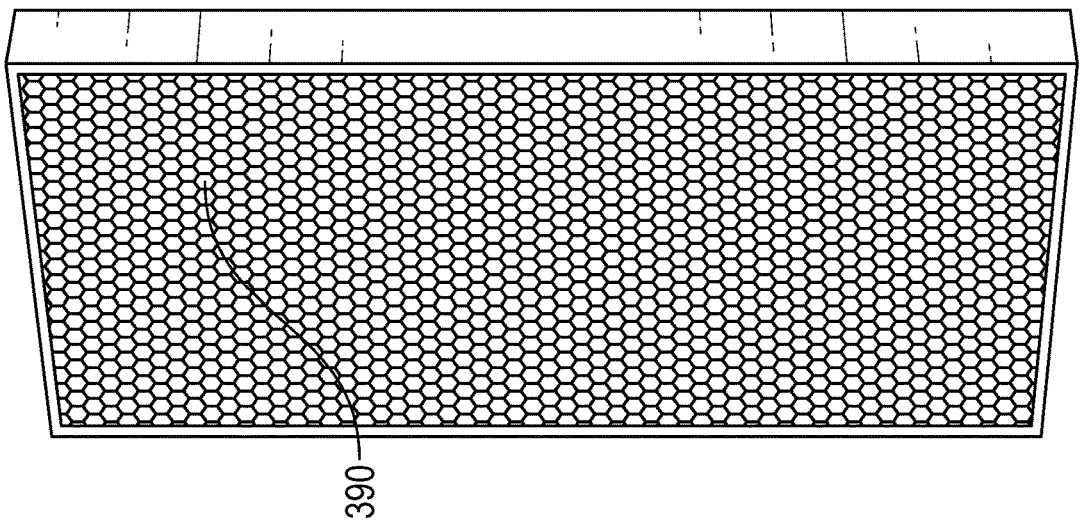
Figure 17C:
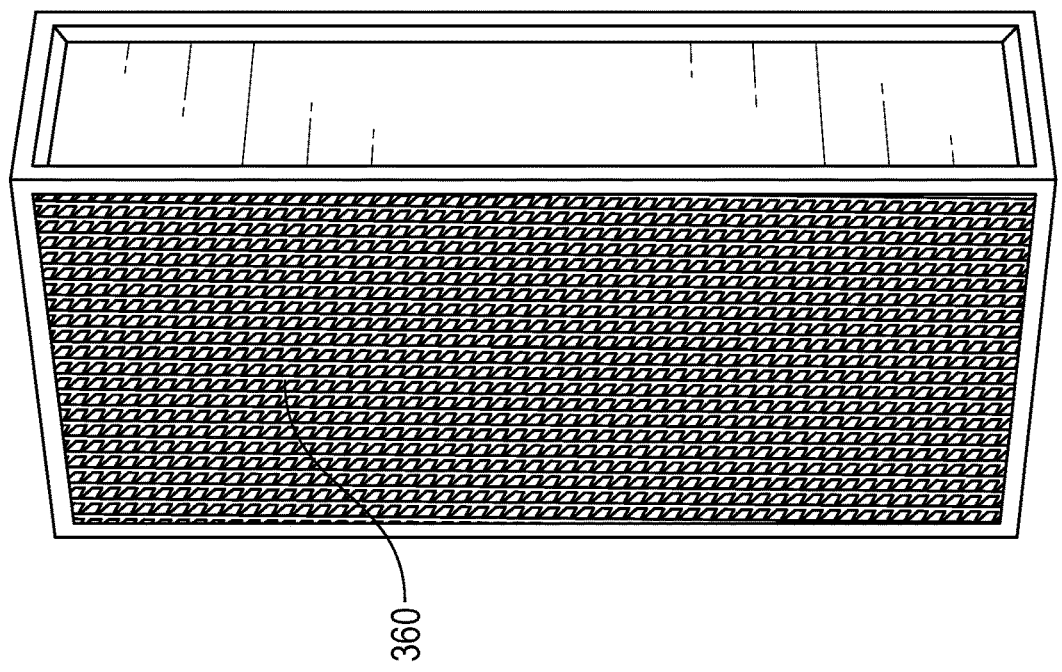
Figure 17B:
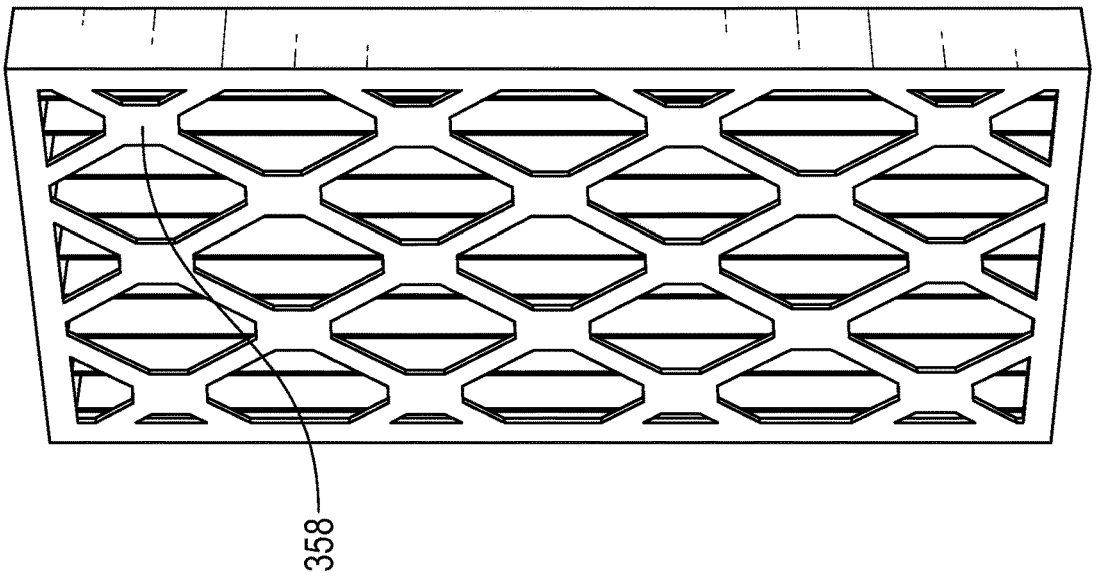
Figure 18:
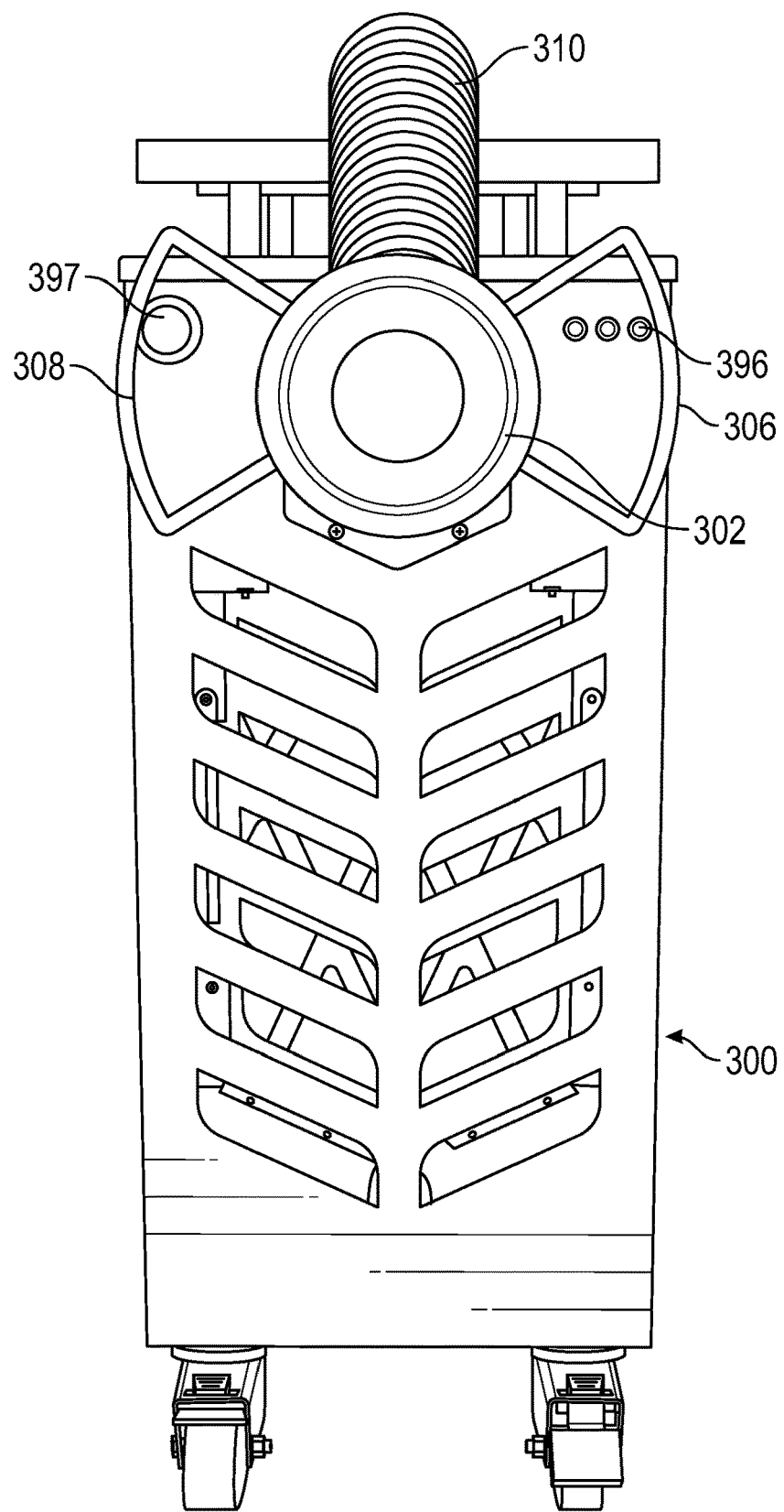
FIGS. 18 and 20 are front views of the air purification system of FIGS. 3-12 in accordance with an illustrative embodiment.
Figure 19B:
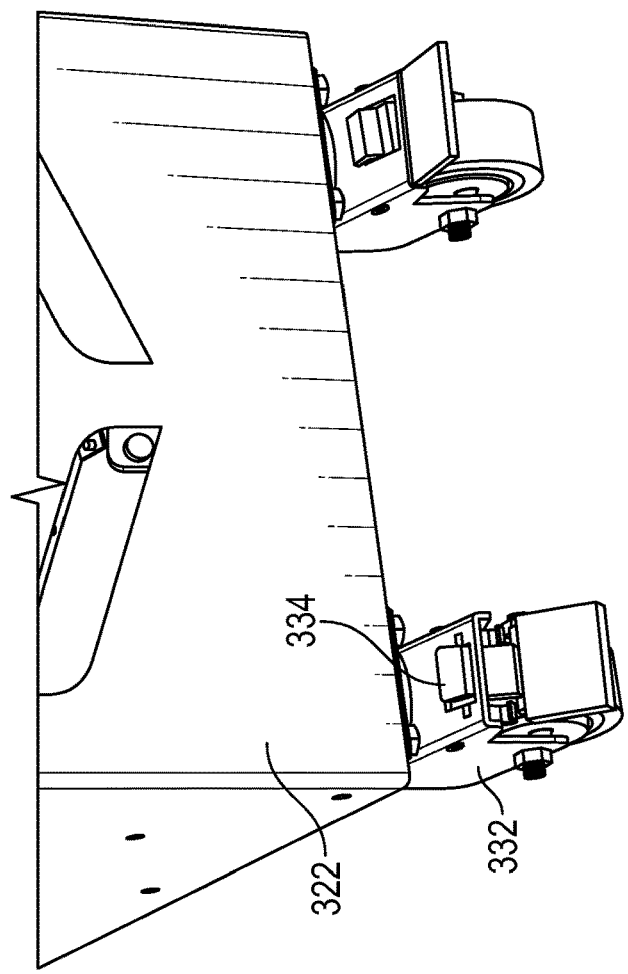
FIGS. 19A-C are perspective views of portions of the front of the air purification system in accordance with an illustrative embodiment.
Figure 19A:
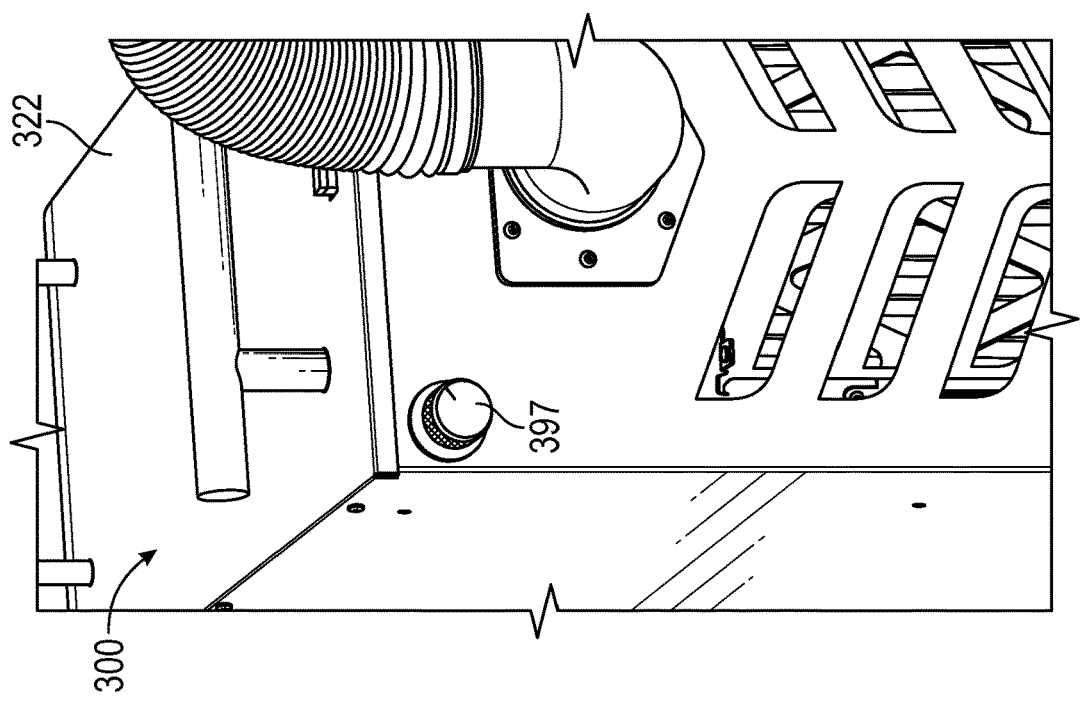
Figure 20:
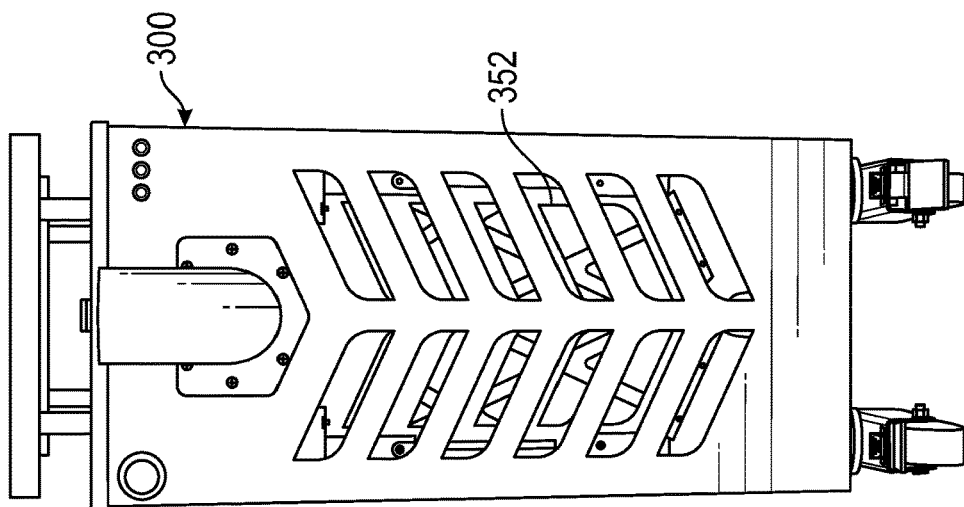
Figure 19C:
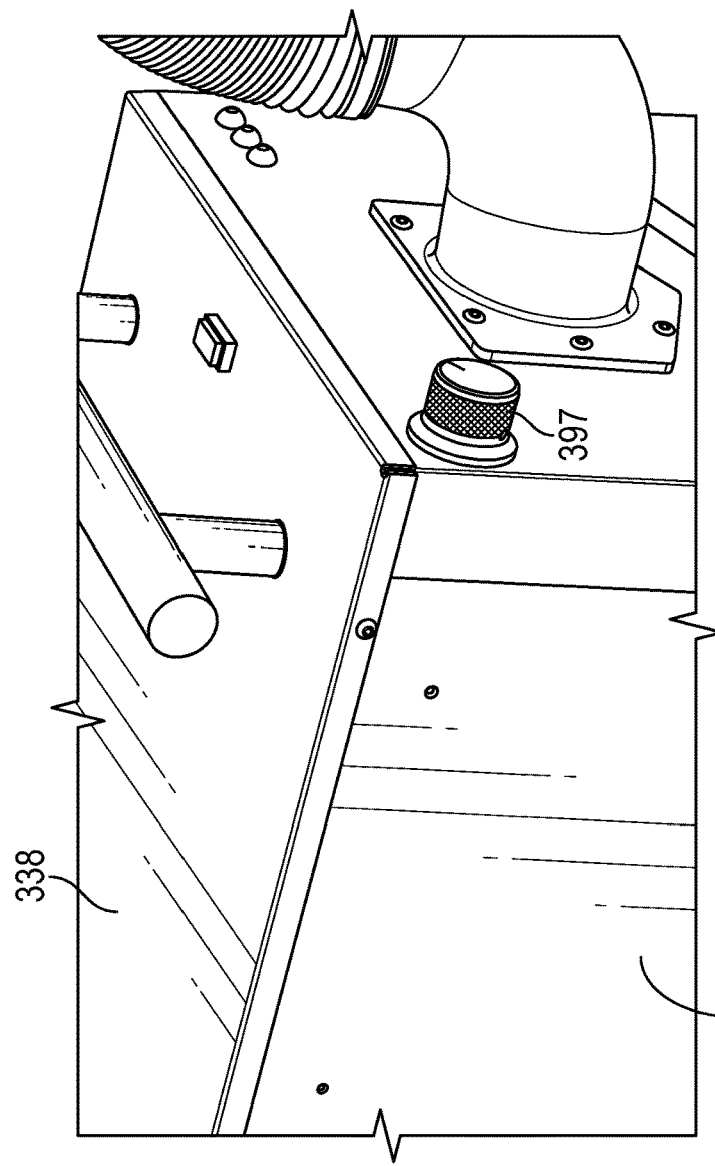
Figure 21:
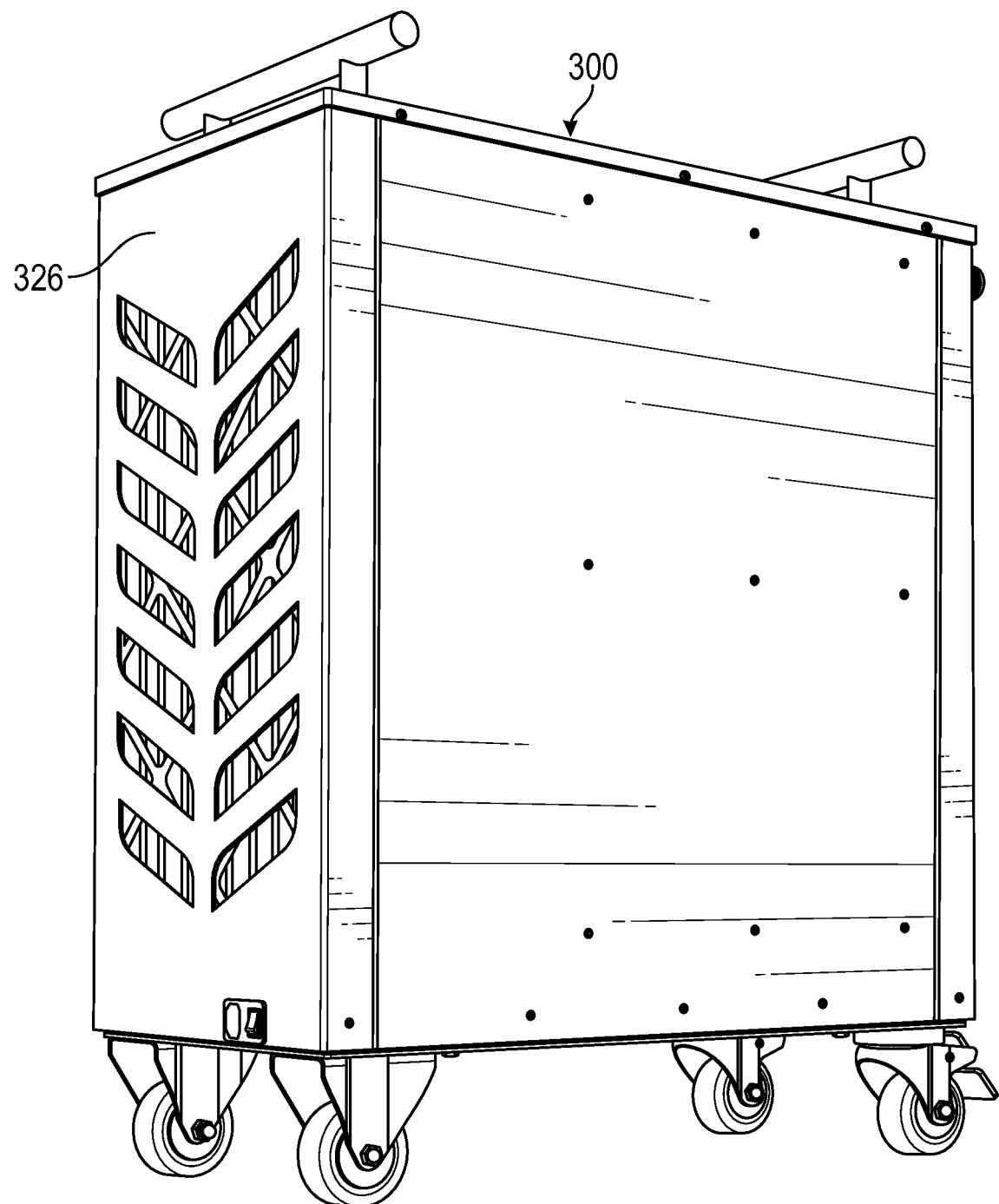
FIG. 21 is a perspective view of the air purification system of FIGS. 3-12 in accordance with an illustrative embodiment.

FIG. 15 depicts a computing system 1500 in accordance with an illustrative embodiment. For example, the computing system 1500 may represent a device, such as one or more of the devices 201 of FIG. 2. The computing system 1500 includes a processor unit 1001 (possibly including multiple processors, multiple cores, multiple nodes, and/or implementing multi-threading, etc.). The computing system includes memory 1007. The memory 1007 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computing system also includes a bus 1003 (e.g., PCI, ISA, PCI-Express, HyperTransport®, InfiniBand®, NuBus, etc.), a network interface 1005 (e.g., an ATM interface, an Ethernet interface, a Frame Relay interface, SONET interface, wireless interface, etc.), and a storage device(s) 1009 (e.g., optical storage, magnetic storage, etc.). The system memory 1007 embodies functionality to implement embodiments described above. The system memory 1007 may include one or more functionalities that store user data (including transactions), content, blockchain data, tokens, ledgers, parameters, application, user profiles, and so forth.

Code may be implemented in any of the other devices of the computing system 1500. Any one of these functionalities may be partially (or entirely) implemented in hardware and/or on the processing unit 1001. For example, the functionality may be implemented with an application specific integrated circuit, in logic implemented in the processing unit 1001, in a co-processor on a peripheral device or card, etc. Further, realizations may include fewer or additional components not illustrated in FIG. 15 (e.g., video cards, audio cards, additional network interfaces, peripheral devices, etc.). The processor unit 1001, the storage device(s) 1009, and the network interface 1005 are coupled to the bus 1003. Although illustrated as being coupled to the bus 1003, the memory 1007 may be coupled to the processor unit 1001.

FIG. 16 is a pictorial representation of the nozzle 302 and intake hose 310 of FIGS. 3-12 in accordance with an illustrative embodiment. As shown, the nozzle 302 may include handles 306, 308 for easily moving the nozzle 302 and associated intake hose 310 into position. The handles 306, 308 may also be referred to as butterfly handles because of their shape and configuration. In one embodiment, the nozzle 302 is formed or coated with antibacterial materials. In another embodiment, the nozzle 302 may include an external UV light for sterilizing the outer surface of the nozzle 302. In another embodiment, the nozzle 302 may include one or more indicators that indicate the direction of the nozzle. For example, lights, lasers, or other projection components may be utilized.

Figure 22:
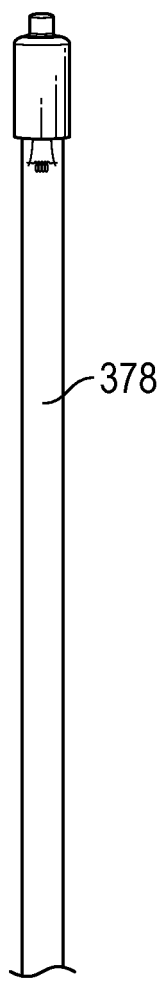
FIG. 22 is a pictorial representation of a bulb in accordance with an illustrative embodiment.

FIG. 22 is a pictorial representation of a VUV bulb 378 in accordance with an illustrative embodiment. The VUV bulb 378 may represent any number of ultraviolet bulbs or lights (e.g., light emitting diode, bulb, lasers, optical resonators, etc.). The VUV bulb 378 may also represent the UVC bulbs or lights herein described.

The features, steps, and components of the illustrative embodiments may be combined in any number of ways and are not limited specifically to those described. In particular, the illustrative embodiments contemplate numerous variations in the smart devices and communications described. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes or methods of the invention. It is understood that any other modifications, substitutions, and/or additions may be made, which are within the intended spirit and scope of the disclosure. For the foregoing, it can be seen that the disclosure accomplishes at least all of the intended objectives.

The illustrative embodiments are not to be limited to the particular embodiments and examples described herein. In particular, the illustrative embodiments contemplate numerous variations in the type of ways in which embodiments of the invention may be applied to air filtering, purification, and sterilization. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes or methods of the invention. It is understood that any other modifications, substitutions, and/or additions may be made, which are within the intended spirit and scope of the disclosure. For the foregoing, it can be seen that the disclosure accomplishes at least all of the intended objectives.

The previous detailed description is of a small number of embodiments for implementing the invention and is not intended to be limiting in scope. The following claims set forth a number of the embodiments disclosed with greater particularity.

What is claimed is:

1. An air purification system, comprising:
a frame housing various components, the frame is mounted to a plurality of casters for moving the filtering device between locations;
an inlet configured to select between vents integrated with the frame and a hose to suction air from an environment, the hose is attachable to the inlet of the frame, the hose includes an internal support to be freely positioned in three-dimensional space for suctioning air from the environment;
a prefilter attached to the inlet for receiving the air from the environment;
a primary filter proximate the prefilter that further filters the air;
a primary reaction chamber housing a vacuum ultraviolet (VUV) light that treats the air and associated contaminants, wherein the primary reaction chamber is cylindrically shaped to maintain the air proximate the VUV light to generate irradiated air;
a secondary reaction chamber interfaces directly with the primary reaction chamber, the secondary reaction chamber housing one or more ultraviolet-C lights for treating the irradiated air to remove ozone generated by the VUV light of the primary reaction chamber and to denature the contaminants;
a fan interfaces with the secondary reaction chamber to move the air through the air purification system; and
a carbon filter interfaces with the fan to remove ozone and contaminants from the irradiated air.

2. The air purification system of claim 1, wherein the hose includes a nozzle with two or more butterfly handles for positioning the hose.

3. The air purification system of claim 2, wherein a moisture control barrier is attached to the nozzle for prefiltering particulates and aerosols.

4. The air purification system of claim 1, wherein the primary filter represents a high-efficiency particulate air (HEPA) filters or ultra-low particulate air (ULPA) filter.

5. The air purification system of claim 1, wherein the primary reaction chamber is housed within the secondary reaction chamber.

6. The air purification system of claim 1, wherein the primary reaction chamber includes multiple openings for dispersing the irradiated air into the secondary reaction chamber, wherein the secondary reaction chamber includes two or more ultraviolet-C lights.

7. The air purification system of claim 1, wherein a diameter and length of the primary reaction chamber are associated with a time period for the air to be treated by the vacuum ultraviolet radiation at approximately 180 nm.

8. The air purification system of claim 7, wherein the time period is at least 0.026 seconds.

9. The air purification system of claim 1, wherein the frame includes a hinged top for easily replacing the prefilter, the primary filter, the VUV light, the ultraviolet-C lights, and the carbon filter.

10. A method for air purification, comprising:
intaking air from an environment into an air purification system through vents or an intake hose in response to activation of a selector configured to select between the vents and the intake hose;
prefiltering the air with a prefilter;
filtering the air with a primary filter to generate filtered air;
treating the filtered air with vacuum ultraviolet radiation in a primary reaction chamber to generate irradiated air;
treating the irradiated air with ultraviolet-C radiation in a secondary reaction chamber directly connected to the primary reaction chamber;
removing ozone and other contaminants from the irradiated air emitted from the secondary reaction chamber utilizing a carbon filter to generate purified air; and
emitting the purified air back into the environment through the air purification system.

11. The method of claim 10, further comprising:
prefiltering the air from the environment receive through the intake hose with a moisture control barrier covering a nozzle, wherein the intake hose includes an internal support for freely positioning the nozzle in three-dimensional space.

12. The method of claim 11, wherein the primary reaction chamber includes at least one vacuum ultraviolet bulb, and wherein the secondary reaction chamber includes at least two ultraviolet-C bulbs.

13. The method of claim 11, wherein the primary filter is a HEPA or ULPA filter.

14. The method of claim 11, wherein the air purification system includes a hinged top for easily replacing the prefilter, the primary filter, ultraviolet bulbs associated with the vacuum ultraviolet radiation and the ultraviolet-C radiation, and the carbon filter.

15. The method of claim 11, further comprising:
catalyzing the irradiated air to remove ozone utilizing one or more catalysts.

16. The method of claim 11, further comprising:
shutting down the ultraviolet irradiation and/or air purification system in response to ozone levels emitted from the air purification system exceeding a threshold.

17. The method of claim 11, wherein the carbon filter includes a catalyst for further removing ozone from the filtered air received from the secondary reaction chamber.

18. The method of claim 11, wherein a diameter and length of the primary reaction chamber are associated with a time period for the air to be treated by the vacuum ultraviolet radiation at approximately 180 nm.

19. The method of claim 11, wherein the primary reaction chamber is within a reaction chamber that also includes the secondary reaction chamber.

20. The method of claim 11, wherein one or more channels divert airflow within the secondary chamber to prolong exposure of the irradiated air to the ultraviolet-C radiation to remove ozone and treat the air for contaminants.

* * * * *